United States Patent
Hindson et al.

(10) Patent No.: US 10,053,723 B2
(45) Date of Patent: *Aug. 21, 2018

(54) CAPSULE ARRAY DEVICES AND METHODS OF USE

(71) Applicant: 10X Genomics, Inc., Pleasanton, CA (US)

(72) Inventors: Benjamin Hindson, Pleasanton, CA (US); Serge Saxonov, Oakland, CA (US); Michael Schnall-Levin, San Francisco, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/719,459

(22) Filed: Sep. 28, 2017

(65) Prior Publication Data

US 2018/0030512 A1    Feb. 1, 2018

Related U.S. Application Data

(60) Continuation of application No. 15/598,898, filed on May 18, 2017, which is a continuation of application No. 14/624,468, filed on Feb. 17, 2015, now Pat. No. 9,689,024, which is a division of application No. 13/966,150, filed on Aug. 13, 2013.

(60) Provisional application No. 61/844,804, filed on Jul. 10, 2013, provisional application No. 61/840,403, filed on Jun. 27, 2013, provisional application No. 61/800,223, filed on Mar. 15, 2013, provisional application No. 61/762,435, filed on Feb. 8, 2013, provisional application No. 61/737,374, filed on Dec. 14, 2012, provisional application No. 61/683,192, filed on Aug. 14, 2012.

(51) Int. Cl.
| | |
|---|---|
| *C12Q 1/6806* | (2018.01) |
| *B01L 3/00* | (2006.01) |
| *B01J 19/00* | (2006.01) |
| *C12N 15/10* | (2006.01) |

(52) U.S. Cl.
CPC ........ *C12Q 1/6806* (2013.01); *B01J 19/0046* (2013.01); *B01L 3/508* (2013.01); *B01L 3/502715* (2013.01); *B01L 3/523* (2013.01); *C12N 15/1065* (2013.01); *B01L 2200/0647* (2013.01); *B01L 2400/0677* (2013.01); *C12Q 2535/122* (2013.01); *C12Q 2563/159* (2013.01)

(58) Field of Classification Search
CPC . C12Q 1/6806; C12N 15/1065; B01J 19/0046
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | Smythe et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,900,481 A | 5/1999 | Lough et al. |
| 5,958,703 A | 9/1999 | Dower et al. |

(Continued)

FOREIGN PATENT DOCUMENTS

| | | |
|---|---|---|
| EP | 0249007 A2 | 12/1987 |
| EP | 0271281 A2 | 6/1988 |

(Continued)

OTHER PUBLICATIONS

Abate, et al. Beating Poisson encapsulation statistics using close-packed ordering. Lab Chip. Sep. 21, 2009;9(18):2628-31. doi: 10.1039/b909386a. Epub Jul. 28, 2009.

(Continued)

*Primary Examiner* — Narayan K Bhat
(74) *Attorney, Agent, or Firm* — Wilson Sonsini Goodrich & Rosati

(57) ABSTRACT

This disclosure provides microwell capsule array devices. The microwell capsule array devices are generally capable of performing one or more sample preparation operations. Such sample preparation operations may be used as a prelude to one more or more analysis operations. For example, a device of this disclosure can achieve physical partitioning and discrete mixing of samples with unique molecular identifiers within a single unit in preparation for various analysis operations. The device may be useful in a variety of applications and most notably nucleic-acid-based sequencing, detection and quantification of gene expression and single-cell analysis.

30 Claims, 4 Drawing Sheets

(56) References Cited

U.S. PATENT DOCUMENTS

| | | |
|---|---|---|
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,986,286 B2 | 3/2015 | Tanghoj et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |

(56) References Cited

U.S. PATENT DOCUMENTS

| | | |
|---|---|---|
| 9,856,530 B2 | 1/2018 | Hindson et al. |
| 9,951,386 B2 | 4/2018 | Hindson et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |

(56) References Cited

U.S. PATENT DOCUMENTS

| | | |
|---|---|---|
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0196288 A1 | 8/2012 | Beer et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0018970 A1 | 1/2013 | Woundy et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0057799 A1 | 2/2014 | Johnson et al. |
| 2014/0065234 A1 | 3/2014 | Shum et al. |
| 2014/0120529 A1 | 5/2014 | Andersen et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0267191 A1 | 9/2015 | Steelman et al. |
| 2015/0298091 A1 | 10/2015 | Weitz et al. |
| 2015/0299772 A1 | 10/2015 | Zhang |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0032282 A1 | 2/2016 | Vigneault et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |

FOREIGN PATENT DOCUMENTS

| | | |
|---|---|---|
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |

(56) References Cited

FOREIGN PATENT DOCUMENTS

| | | |
|---|---|---|
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| WO | WO-8402000 A1 | 5/1984 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009048532 A2 | 4/2009 |
| WO | WO-2009061372 A1 | 5/2009 |
| WO | WO-2009085215 A1 | 7/2009 |
| WO | WO-2010004018 A2 | 1/2010 |
| WO | WO-2010033200 A2 | 3/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011140627 A1 | 11/2011 |
| WO | WO-2012012037 A1 | 1/2012 |
| WO | WO-2012047889 A2 | 4/2012 |
| WO | WO-2012048341 A1 | 4/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO 2012/136734 * | 10/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2014028537 A1 | 2/2014 |
| WO | WO-2014053854 A1 | 4/2014 |
| WO | WO-2014071361 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014144495 A1 | 9/2014 |
| WO | WO-2014210353 A2 | 12/2014 |
| WO | WO-2015044428 A1 | 4/2015 |
| WO | WO-2015164212 A1 | 10/2015 |
| WO | WO-2016040476 A1 | 3/2016 |
| WO | WO-2016126871 A2 | 8/2016 |
| WO | WO-2016191618 A1 | 12/2016 |
| WO | WO-2017015075 A1 | 1/2017 |
| WO | WO-2017025594 A1 | 2/2017 |
| WO | WO-2017053905 A1 | 3/2017 |
| WO | WO-2017075265 A1 | 5/2017 |

OTHER PUBLICATIONS

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

(56) References Cited

OTHER PUBLICATIONS

Abate et al., Valve-based flow focusing for drop formation. Appl Phys Lett. 2009;94. 3 pages.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Ahern, "Biochemical, Reagents Kits Offer Scientists Good Return on Investment" The Scientist (1995) 9(15):1-7.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Biol., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna, S.L., et al., "Formation of dispersions using "flow focusing" in microchannels," Applied Physics Letters, vol. 82, No. 3, pp. 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB2886981354/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone Pcr. Nucl. Acids Res. 32(22):e176 2004.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb 2002; 78A-86A.
Boulanger, et al, "Massively parallel haplotyping on microscopic beads for the high-throughput phase analysis of single molecules", PLoS One, vol. 7:1-10, 2012.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Biol. Therp., 4:11 1821-1829 (2004).
Casbon, et al, "Reflex: intramolecular barcoding of long-range PCR products for sequencing multiple pooled DNAs", Nucleic Acids Res., pp. 1-6, 2013.
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;I8(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics. 2010;186:757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. Feb. 15, 2013;339(6121):819-23. doi: 10.1126/science.1231143. Epub Jan. 3, 2013.

(56) References Cited

OTHER PUBLICATIONS

Cook, et al. Copy-number variations associated with neuropsychiatric conditions. Nature. Oct. 16, 2008;455(7215):919-23. doi: 10.1038/nature07458.
Co-pending U.S. Appl. No. 15/392,557, filed Dec. 28, 2016.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/470,814, filed Mar. 27, 2017.
Co-pending U.S. Appl. No. 15/596,754, filed May 16, 2017.
Co-pending U.S. Appl. No. 15/598,898, filed May 18, 2017.
Co-pending U.S. Appl. No. 15/687,357, filed Aug. 25, 2017.
Co-pending U.S. Appl. No. 15/687,856, filed Aug. 28, 2017.
Co-pending U.S. Appl. No. 15/717,840, filed Sep. 27, 2017.
Co-pending U.S. Appl. No. 15/717,847, filed Sep. 27, 2017.
Co-pending U.S. Appl. No. 15/717,871, filed Sep. 27, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/720,085, filed Sep. 29, 2017.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Dekker, et al. Capturing chromosome conformation. Science. Feb. 15, 2002;295(5558):1306-11.
Demirci, et al. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. doi: 10.1073/pnas.0808319105. Epub Oct. 6, 2008.
Fan, et al. Whole-genome molecular haplotyping of single cells. Nature Biotechnology, vol. 29, No. 1. Jan. 1, 2011. pp. 51-57.

Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fulton et al., Advanced multiplexed analysis with the FlowMetrix system. Clin Chem. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Han, X. et al. "CRISPR-Cas9 delivery to hard-to-transfect cells via membrane deformation" Science Advances (2015) 1(7): E1500454 (8 pages).
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He et al., "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008.

(56) References Cited

OTHER PUBLICATIONS

Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to the University of Birmingham for the degree of Doctor of Philosophy. 2009.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. Jul. 2, 1999;285(5424):83-5.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly( ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioj, et al., "Counting Absolute Numbers of Molecules Using Unique Molecular Identifiers", Nature Methods 9, 72-74 (2012).
Klein, et al. Droplet barcoding for single-cell transcriptomics applied to embryonic stem cells. Cell. May 21, 2015;161(5):1187-201. doi: 10.1016/j.cell.2015.04.044.
Knight, et al. Subtle chromosomal rearrangements in children with unexplained mental retardation. Lancet. Nov. 13, 1999;354(9191):1676-81.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip the Royal Soc. of Chem. 8: 1110-1115 (2008).
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kutyavin, et al. Oligonucleotides containing 2-aminoadenine and 2-thiothymine act as selectively binding complementary agents. Biochemistry. Aug. 27, 1996;35(34):11170-6.
Kwok, et al, "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Laird et al, Hairpin-bisulfite PCR: Assessing epigenetic methylation patterns on complementary strands of individual DNA molecules, 2004, PNAS, 101, 204-209.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee, et al., "Highly multiplexed subcellular RNA sequencing in situ. Science. Mar. 21, 2014;343(6177):1360-3. doi: 10.1126/science.1250212. Epub Feb. 27, 2014."
Lee, J-H. et al. "Fluorescent in situ sequencing (FISSEQ) of RNA for gene expression profiling in intact cells and tissues" Nature Protocols (Feb. 12, 2015) 10(3):442-458.
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).

(56) References Cited

OTHER PUBLICATIONS

Lowe, Adam J. Norbornenes and [n]polynorbornanes as molecular scaffolds for anion recognition. Ph.D. Thesis (May 2010). (361 pages).
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Man. Monolithic Structures for Integrated Microfluidic Analysis. PhD Thesis. 2001.
Marcus. Gene method offers diagnostic hope. The Wall Street Journal. Jul. 11, 2012.
Maricic T, et al. Optimization of 454 sequencing library preparation from small amounts of DNA permits sequence determination of both DNA strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Miller JC, et al. An improved zinc-finger nuclease architecture for highly specific genome editing. Nat. Biotechnol. 2007;25:778-785.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Novak, et al. Single cell multiplex gene detection and sequencing using microfluidically-generated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production of Monodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Oyola, et al, "Optimizing Illumina next-generation sequencing library preparation for extremely AT-biased genomes", BMC Genomics.,13:1, 2012.
Pantel, et al. Detection methods of circulating tumor cells. J Thorac Dis. Oct. 2012;4(5):446-7. doi: 10.3978/j.issn.2072-1439.2012.08.15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, et al. Accurate whole-genome sequencing and haplotyping from 10 to 20 human cells. Nature. Jul. 11, 2012;487(7406):190-5. doi: 10.1038/Nature11236.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Porteus MH, Baltimore D. Chimeric nucleases stimulate gene targeting in human cells. Science. 2003;300:763.
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran, et al., Genome Engineering Using the CRISPR-Cas9 System, Nature Protocol, (2013), 8(11):2281-2308.
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.

(56) References Cited

OTHER PUBLICATIONS

Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 UsingMultiplexIdentifier-AdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptors-ForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sander JD, et al. Selection-free zinc-finger-nuclease engineering by context-dependent assembly (CoDA). Nat. Methods. 2011;8:67-69.
Schirinzi et al., Combinatorial sequencing-by-hybridization: Analysis of the NF1 gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci USA. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Skerra A. Phosphorothioate primers improve the amplification of DNA sequences by DNA polymerases with proofreading activity. Nucleic Acids Res. Jul. 25, 1992; 20(14):3551-4.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Tawfik, D.S., et al., "Man-made cell-like compartments for molecular evolution," Nature Biotechnology, vol. 16, pp. 652-656 (1998).
Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.

(56) References Cited

OTHER PUBLICATIONS

Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams et al., Amplification of complex gene libraries by emulsion PCR, Nature Methods 3(7):545-550 (2006).
Wiseman, R.W. et al. "Major histocompatibility complex genotyping with massively parallel pyrosequencing" Nature Medicine (Oct. 11, 2009) 15(11):1322-1326.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone.0181163. eCollection 2017.
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Hum• Antibodies Hybridomas. Jan. 1992;3(1 ): 14-8.
Zong, et al. Genome-wide detection of single-nucleotide and copy-number variations of a single human cell. Science. Dec. 21, 2012;338(6114):1622-6. doi: 10.1126/science.1229164.
Co-pending U.S. Appl. No. 15/693,374, filed Aug. 31, 2017.
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-ce11-3-solution-utilized-perturb-seq-approach/.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adey, et al. Rapid, low-input, low-bias construction of shotgun fragment libraries by high-density in vitro transposition. Genome Biology 11:R119 (2010).
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Clark, et al. Single-cell epigenomics: powerful new methods for understanding gene regulation and cell identity. Genome Biol. Apr. 18, 2016;17:72. doi: 10.1186/513059-016-0944-x.
Co-pending U.S. Appl. No. 15/825,740, filed Nov. 29, 2017.
Co-pending U.S. Appl. No. 15/831,726, filed Dec. 5, 2017.
Co-pending U.S. Appl. No. 15/831,847, filed Dec. 5, 2017.
Co-pending U.S. Appl. No. 15/832,183, filed Dec. 5, 2017.
Co-pending U.S. Appl. No. 15/832,547, filed Dec. 5, 2017.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.

(56) References Cited

OTHER PUBLICATIONS

Co-pending U.S. Appl. No. 15/847,659, filed Dec. 19, 2017.
Co-pending U.S. Appl. No. 15/847,752, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Co-pending U.S. Appl. No. 15/875,899, filed Jan. 19, 2018.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Hamilton, A.J. "microRNA in erythrocytes" Biochem. Soc. Trans. (2010) 38, 229-231.
Lake, et al. "Integrative Single-Cell Analysis by Transcriptional and Epigenetic States in Human Adult Brain". Apr. 19, 2017. doi: https://doi.org/10.1101/128520.
Lennon; et al., "Lennon et al. A scalable, fully automated process for construction of sequence-ready barcoded libraries for 454. Genome Biology 11:R15 (2010)."
Macaulay; et al., "G&T-seq: parallel sequencing of single-cell genomes and transcriptomes. Nature Methods, 2015, p. 1-7."
Macaulay, et al. Single-Cell Multiomics: Multiple Measurements from Single Cells. Trends in Genetics 33.2 (2017): 155-168. PMC. Web. Dec. 18, 2017.
miRNA (http://www.exiqon.com/what-are-microRNAs) accessed Oct. 19, 2017.
Orakdogen, N. "Novel responsive poly(N,N-dimethylaminoethyl methacrylate) gel beads: preparation, mechanical properties and pH-dependent swelling behavior" J Polym Res (2012) 19:9914.
"Portable Water Filters" (http://www.portablewaterfilters.org/water-filter-guide/particle-contaminant-size-chart-microns/) 2015, accessed Oct. 19, 2017.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Syed, et al. Next-generation sequencing library preparation: simultaneous fragmentation and tagging using in vitro transposition. Nature Methods 2 pgs (Nov. 2009).
Adamson et al., "Production of arrays of chemically distinct nanolitre plugs via repeated splitting in microfluidic devices", Lab Chip 6(9): 1178-1186 (Sep. 2006).
Brenner, et al. In vitro cloning of complex mixtures of DNA on microbeads: physical separation of differentially expressed cDNAs. Proc Natl Acad Sci U S A. Feb. 15, 2000;97(4):1665-70.
Chang et al. Droplet-based microfluidic platform platform for heterogeneous enzymatic assays, 2013, Lab Chip, 13, 1817-1822 (Year: 2013).
Co-pending U.S. Appl. No. 15/887,711, filed Feb. 2, 2018.
Co-pending U.S. Appl. No. 15/887,947, filed Feb. 2, 2018.
Fu, et al. A Microfabricated Fluorescence-Activated Cell Sorter. Nature Biotechnology.1999; 17:1109-1111.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Kolodeziejczyk et al., "The technology and biology of single-cell RNA sequencing", Molecular Cell, vol. 58 (May 21, 2015).
Lasken, et al. (1996) Archaebacterial DNA Polymerases Tightly Bind Uracil-containing DNA. The Journal of Biological Chemistry, 271(30):17692-17696 (Year: 1996).
Lee et al. Alginate: Properties and biomedical applications. Prog Polym Sci 37(1):106-126 (2012).
Miller-Stephenson Chemicals 157 FS Series catalog, www.miller-stephenon.com.
Morimoto, et al. Monodisperse semi-permeable microcapsules for continuous observation of cells. 2009. Lab Chip 9(15):2217-2223.
Narayanan, J. et al. "Determination of agarose gel pore size: Absorbance measurements vis a vis other techniques" Journal of Physics: Conference Series 28 (2006) 83-86 (Year: 2006).
Sakaguchi, et al. (1996) Cautionary Note on the Use of dUMP-Containing PCR Primers with Pfu and VentR. Biotechniques, 21(3): 369-370 (Year: 1996).
Spormann Laboratory, Polymerase Chain Reaction (PCR), Alfred Spormann Laboratory, 2009, 1-3. (Year: 2009).
ThermoFisher, Protocols, M-270 Streptavidin, ThermoFisherScientific, 2007, 1-5. (Year: 2007).
Xia and Whitesides, Soft Lithography, Angew. Chem. Int. Ed. 37:550-575 (1998).
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Wong, et al. Multiplexed Barcoded CRISPR-Cas9 Screening Enabled by CombiGEM. PNAS. Mar. 1, 2016, vol. 113, pp. 2544-2549.
Co-pending U.S. Appl. No. 15/933,299, filed Mar. 22, 2018.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.

* cited by examiner

CAPSULE ARRAY DEVICES AND METHODS OF USE

CROSS-REFERENCE

This application is a continuation of U.S. application Ser. No. 15/598,898, filed May 18, 2017, which is a continuation of U.S application Ser. No. 14/624,468, filed Feb. 17, 2015, which is a divisional of U.S. Patent application Ser. No. 13/966,150, filed Aug. 13, 2013, which applications claim the benefit of U.S. Provisional Patent Application No. 61/844,804, filed Jul. 10, 2013, U.S. Provisional Patent Application No. 61/840,403, filed Jun. 27, 2013, U.S. Provisional Patent Application No. 61/800,223, filed Mar. 15, 2013, U.S. Provisional Patent Application No. 61/762,435, filed Feb. 8, 2013, U.S. Provisional Patent Application No. 61/737,374, filed Dec. 14, 2012, and U.S. Provisional Patent Application No. 61/683,192, filed Aug. 14, 2012, each of which is entirely incorporated herein by reference for all purposes.

BACKGROUND OF THE INVENTION

The detection and quantification of analytes is important for molecular biology and medical applications such as diagnostics. Genetic testing is particularly useful for a number of diagnostic methods. For example, disorders that are caused by mutations, such as cancer, may be detected or more accurately characterized with DNA sequence information.

Appropriate sample preparation is often needed prior to conducting a molecular reaction such as a sequencing reaction. A starting sample may be a biological sample such as a collection of cells, tissue, or nucleic acids. When the starting material is cells or tissue, the sample may need to be lysed or otherwise manipulated in order to permit the extraction of molecules such as DNA. Sample preparation may also involve fragmenting molecules, isolating molecules, and/or attaching unique identifiers to particular fragments of molecules, among other actions. There is a need in the art for improved methods and devices for preparing samples prior to downstream applications.

SUMMARY OF THE INVENTION

This disclosure provides compositions and methods for a microcapsule array device.

An aspect of the disclosure provides a composition comprising a first microcapsule, wherein: the first microcapsule is degradable upon the application of a stimulus to the first microcapsule; and the first microcapsule comprises an oligonucleotide barcode. In some cases, the first microcapsule may comprise a chemical cross-linker. The chemical cross-linker, for example, may be a disulfide bond. In some cases, the composition may comprise a polymer gel, such as, for example a polyacrylamide gel. The first microcapsule may comprise a bead. In some cases, the bead may be a gel bead.

Moreover, the stimulus may be selected from the group consisting of a biological, chemical, thermal, electrical, magnetic, or photo stimulus, and combination thereof. In some cases, the chemical stimulus may be selected from the group consisting of a change in pH, a change in ion concentration, and a reducing agent. The reducing agent may be, for example, dithiothreitol (DTT) or tris(2-carboxyethyl) phosphine (TCEP).

A second microcapsule may comprise the first microcapsule. Moreover, the second microcapsule may be a droplet. In some cases, the composition may also comprise a nucleic acid that comprises the oligonucleotide barcode, wherein the nucleic acid comprises a deoxyuridine triphosphate (dUTP). In some cases, the composition may comprise a polymerase unable to accept a deoxyuridine triphosphate (dUTP). Also, the composition may comprise a target analyte, such as, for example, a nucleic acid. The nucleic acid may be selected from the group consisting of DNA, RNA, dNTPs, ddNTPs, amplicons, synthetic nucleotides, synthetic polynucleotides, polynucleotides, oligonucleotides, peptide nucleic acids, cDNA, dsDNA, ssDNA, plasmid DNA, cosmid DNA, High Molecular Weight (MW) DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA. In some cases, the nucleic acid may be genomic DNA (gDNA).

Additionally, the density of the oligonucleotide barcodes may be at least about 1,000,000 oligonucleotide barcodes per the first microcapsule. The oligonucleotide barcode may be coupled to the microcapsule via a chemical cross-linker, such as, for example a disulfide bond.

An additional aspect of the disclosure comprises a device comprising a plurality of partitions, wherein: at least one partition of the plurality of partitions comprises a microcapsule comprising an oligonucleotide barcode; and the microcapsule is degradable upon the application of a stimulus to the microcapsule. The partition, for example, may be a well or a droplet. In some cases, the microcapsule comprises a chemical cross-linker such as, for example, a disulfide bond. Moreover, the microcapsule may comprise a polymer gel such as, for example, a polyacrylamide gel. Also, the microcapsule may comprise a bead. In some cases, the bead may be a gel bead.

The stimulus may be selected from the group consisting of a biological, chemical, thermal, electrical, magnetic, or photo stimulus, and a combination thereof. In some cases, the chemical stimulus may be selected from the group consisting of a change in pH, change in ion concentration, and a reducing agent. The reducing agent, for example, may be dithiothreitol (DTT) or tris(2-carboxyethyl) phosphine (TCEP).

Furthermore, a nucleic acid may comprise the oligonucleotide barcode and the nucleic acid may comprise a deoxyuridine triphosphate (dUTP). In some cases, the partition may comprise a polymerase unable to accept a deoxyuridine triphosphate (dUTP). Additionally, the partition may comprise a target analyte such as, for example, a nucleic acid. The nucleic acid may be selected from the group consisting of DNA, RNA, dNTPs, ddNTPs, amplicons, synthetic nucleotides, synthetic polynucleotides, polynucleotides, oligonucleotides, peptide nucleic acids, cDNA, dsDNA, ssDNA, plasmid DNA, cosmid DNA, High Molecular Weight (MW) DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA. In some cases, the nucleic acid may be genomic DNA (gDNA). The oligonucleotide barcode may be coupled to the microcapsule via a chemical cross-linker. In some cases, the chemical cross-linker may be a disulfide bond.

A further aspect of the disclosure provides a method for sample preparation comprising combining a microcapsule comprising an oligonucleotide barcode and a target analyte into a partition, wherein the microcapsule is degradable upon the application of a stimulus to the microcapsule; and applying the stimulus to the microcapsule to release the oligonucleotide barcode to the target analyte. The partition may be, for example, a well or a droplet. In some cases, the microcapsule may comprise a polymer gel such as, for example, a polyacrylamide. Moreover, the microcapsule may comprise a bead. In some cases, the bead may be a gel bead. Moreover, the microcapsule may comprise a chemical cross-linker such as, for example, a disulfide bond.

The stimulus may be selected from the group consisting of a biological, chemical, thermal, electrical, magnetic, photo stimulus, and a combination thereof. In some cases, the chemical stimulus may be selected from the group consisting of a change in pH, change in ion concentration, and a reducing agent. The reducing agent may be, for example, dithiothreitol (DTT) or tris(2-carboxyethyl) phosphine (TCEP).

Also, a nucleic acid may comprise the oligonucleotide barcode and the nucleic acid may comprise a deoxyuridine triphosphate (dUTP). In some cases, the partition may comprise a polymerase unable to accept a deoxyuridine triphosphate (dUTP). Moreover, the method may also comprise attaching the oligonucleotide barcode to the target analyte. The attaching may be completed, for example, with a nucleic acid amplification reaction. Moreover, the analyte may be a nucleic acid. In some cases, the nucleic acid may be selected from the group consisting of DNA, RNA, dNTPs, ddNTPs, amplicons, synthetic nucleotides, synthetic polynucleotides, polynucleotides, oligonucleotides, peptide nucleic acids, cDNA, dsDNA, ssDNA, plasmid DNA, cosmid DNA, High Molecular Weight (MW) DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA. In some cases, the nucleic acid may be genomic DNA (gDNA). Furthermore, the oligonucleotide barcode may be coupled to the microcapsule via a chemical cross-linker. In some cases, the chemical cross-linker may be a disulfide bond.

A further aspect of the disclosure provides a composition comprising a degradable gel bead, wherein the gel bead comprises at least about 1,000,000 oligonucleotide barcodes. In some cases, the 1,000,000 oligonucleotide barcodes are identical.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

BRIEF DESCRIPTION OF THE DRAWINGS

The novel features of a device of this disclosure are set forth with particularity in the appended claims. A better understanding of the features and advantages of this disclosure will be obtained by reference to the following detailed description that sets forth illustrative embodiments, in which the principles of a device of this disclosure are utilized, and the accompanying drawings of which:

DETAILED DESCRIPTION OF THE INVENTION

Figure 1A:
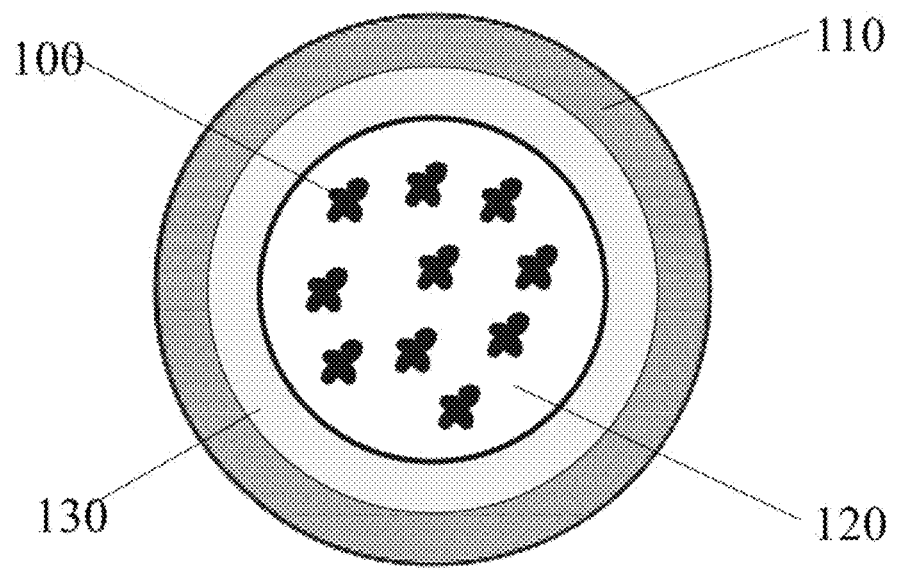
FIG. 1A is a schematic representation of a microcapsule or inner reagent droplet.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

I. General Overview

The present disclosure provides microwell or other partition capsule array devices and methods of using such devices. Generally, the device is an assembly of partitions (e.g., microwells, droplets) that are loaded with microcapsules, often at a particular concentration of microcapsules per partition.

The devices may be particularly useful to perform sample preparation operations. In some cases, a device subdivides a sample (e.g., a heterogeneous mixture of nucleic acids, a mixture of cells, etc.) into multiple partitions such that only a portion of the sample is present in each partition. For example, a nucleic acid sample comprising a mixture of nucleic acids may be partitioned such that no more than one strand of (or molecule of) nucleic acid is present in each partition. In other examples, a cell sample may be partitioned such that no more than one cell is present in each partition.

Following the partitioning step, any of a number of different operations may be performed on the subdivided sample within the device. The partitions may include one or more capsules that contain one or more reagents (e.g., enzymes, unique identifiers (e.g., bar codes), antibodies, etc.). In some cases, the device, a companion device or a user provides a trigger that causes the microcapsules to release one or more of the reagents into the respective partition. The release of the reagent may enable contact of the reagent with the subdivided sample. For example, if the reagent is a unique identifier such as a barcode, the sample may be tagged with the unique identifier. The tagged sample may then be used in a downstream application such as a sequencing reaction.

A variety of different reactions and/operations may occur within a device disclosed herein, including but not limited to: sample partitioning, sample isolation, binding reactions, fragmentation (e.g., prior to partitioning or following partitioning), ligation reactions, and other enzymatic reactions. The device also may be useful for a variety of different molecular biology applications including, but not limited to, nucleic acid sequencing, protein sequencing, nucleic acid quantification, sequencing optimization, detecting gene expression, quantifying gene expression, and single-cell analysis of genomic or expressed markers. Moreover, the device has numerous medical applications. For example, it may be used for the identification, detection, diagnosis, treatment, staging of, or risk prediction of various genetic and non-genetic diseases and disorders including cancer.

II. Microcapsules

FIG. 1A is a schematic of an exemplary microcapsule comprising an internal compartment 120 enveloped by a second layer 130, which is encapsulated by a solid or semi-permeable shell or membrane 110. In general, the shell separates the internal compartment(s) from their immediate environment (e.g., interior of a microwell). The internal compartments, e.g., 120, 130, may comprise materials such as reagents. As depicted in FIG. 1A, the reagents 100 may be present in the internal compartment 120. However, in some cases, the reagents are located in the enveloping layer 130 or in both compartments. Generally, the microcapsule may release the inner materials, or a portion thereof, following the introduction of a particular trigger. The trigger may cause disruption of the shell layer 110 and/or the internal enveloping layer 130, thereby permitting contact of the internal compartment 100, 120 with the outside environment, such as the cavity of a microwell.

The microcapsule may comprise several fluidic phases and may comprise an emulsion (e.g. water-in-oil emulsion, oil-in-water emulsion). A microcapsule may comprise an internal layer 120 that is immiscible with a second layer 130 enveloping the internal layer. For example, the internal layer 120 may comprise an aqueous fluid, while the enveloping layer 130 may be a non-aqueous fluid such as an oil. Conversely, the internal layer 120 may comprise a non-aqueous fluid (e.g., oil), and the enveloping layer 130 may comprise an aqueous fluid. In some cases, the microcapsule does not comprise an enveloping second layer. Often, the microcapsule is further encapsulated by a shell layer 110, which may comprise a polymeric material. In some cases, a microcapsule may comprise a droplet.

Droplets and methods for droplet generation, for example, are described in U.S. Pat. No. RE41,780, which is incorporated herein by reference in its entirety for all purposes. The device also may contain a microfluidic element that enables the flow of a sample and/or microcapsules through the device and distribution of the sample and/or microcapsules within the partitions.

The microcapsule can comprise multiple compartments. The microcapsule may comprise at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 compartments. In other cases, the microcapsule comprises less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 compartments. Similarly, each compartment, or a subset thereof, may also be subdivided into a plurality of additional compartments. In some cases, each compartment, or subset thereof, is subdivided into at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 compartments. In other cases, each compartment, or subset thereof, is further subdivided into less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 compartments.

There are several possible distributions of reagent in the multiple compartments. For example, each compartment (or some percentage of the total number of compartments) may comprise the same reagent or the same combination or reagents. In some cases, each compartment (or some percentage of the total number of compartments) comprises different reagents or a different combination of reagents.

The compartments may be configured in a variety of ways. In some cases, the microcapsule may comprise multiple concentric compartments (repeating units of compartments that contain the preceding compartment), often separated by an immiscible layer. In such microcapsules, the reagents may be present in alternating compartments, in every third compartment, or in every fourth compartment.

Figure 1B:
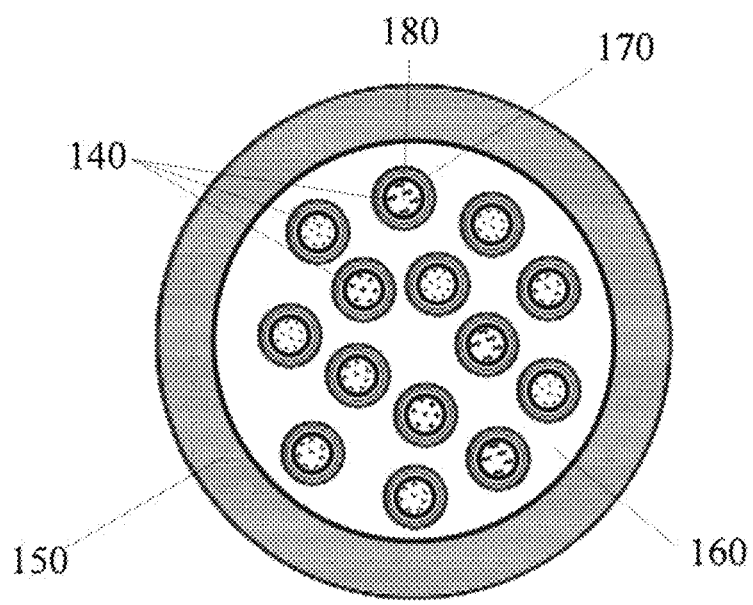
FIG. 1B is a schematic representation of a microcapsule containing multiple inner reagent droplets.

In some cases, most of the compartments with a microcapsule are not concentric; instead, they exist as separate, self-contained entities within a microcapsule. FIG. 1B depicts an example of a microcapsule that contains a plurality of smaller microcapsules 140, each containing a reagent. Like many of the other microcapsules described herein, the microcapsule may be encapsulated by an outer shell, often comprising a polymer material 150. The plurality of smaller microcapsules encapsulated within the larger microcapsule may be physically separated by an immiscible fluid 160, thereby preventing mixing of reagents before application of a stimulus and release of reagents into solution. In some cases, the immiscible fluid is loaded with additional materials or reagents. In some cases, the plurality of smaller microcapsules are surrounded by a layer of immiscible fluid (e.g., 170) which is further surrounded by a fluid 160 that is miscible with the inner fluid of the microcapsules. For example, the interior microcapsules 180 may comprise an aqueous interior enveloped by an immiscible (e.g., oil) layer, that is further surrounded by an aqueous layer 160. The miscible compartments (e.g., 160 and 180) may each contain reagents. They may contain the same reagents (or the same combination of reagents) or different reagents (or different combination of reagents). Alternatively, one or some of the miscible compartments may comprise no reagents.

The microcapsule may comprise a polymeric shell (see, e.g., FIGS. 1 and 2) or multiple polymeric shells. For example, the microcapsule may comprise multiple polymeric shells layered on top of each other. In other cases, individual compartments within a microcapsule comprise a polymeric shell, or a subset of the compartments may comprise a polymeric shell. For example, all or some of the smaller compartments 140 in FIG. 1B may comprise a polymeric shell that separates them from the fluidic interior 160. The microcapsule may be designed so that a particular reagent is contained within a compartment that has a polymerized shell, while a different reagent is within a compartment that is simply enveloped by an immiscible liquid. For example, a reagent that is desired to be released upon a heat trigger may be contained within the compartments that have a heat-sensitive or heat-activatable polymerized shell, while reagents designed to be released upon a different trigger may be present in different types of compartments. In another example, paramagnetic particles may be incorporated into the capsule shell wall. A magnet or electric field may then be used to position the capsule to a desired location. In some cases, a magnetic field (e.g., high frequency alternating magnetic field) can be applied to such capsules; the incorporated paramagnetic particles may then transform the energy of the magnetic field into heat, thereby triggering rupture of the capsule.

The microcapsule component of a device of this disclosure may provide for the controlled and/or timed release of reagents for sample preparation of an analyte. Microcapsules may be used in particular for controlled release and transport of varying types of chemicals, ingredients, pharmaceuticals, fragrances etc . . . , including particularly sensitive reagents such as enzymes and proteins (see, e.g., D. D. Lewis, "Biodegradable Polymers and Drug Delivery Systems", M. Chasin and R. Langer, editors (Marcel Decker, New York, 1990); J. P. McGee et al., J. Control. Release 34 (1995), 77).

Microcapsules may also provide a means for delivery of reagents in discrete and definable amounts. Microcapsules may be used to prevent premature mixing of reagents with the sample, by segregating the reagents from the sample. Microcapsules also may ease handling of—and limit contacts with—particularly sensitive reagents such as enzymes, nucleic acids and other chemicals used in sample preparation.

A. Preparation of Microcapsules

Microcapsules of a device of this disclosure may be prepared by numerous methods and processes. Preparative techniques may include pan coating, spray drying, centrifugal extrusion, emulsion-based methods, and/or microfluidic techniques. Typically, a method for preparation is chosen based on the desired characteristics of the microcapsule. For example, shell wall thickness, permeability, chemical composition of the shell wall, mechanical integrity of the shell wall and capsule size may be taken into consideration when choosing a method. Methods of preparation may also be selected based on the ability to incorporate specific materials within the capsule such as whether the core materials (e.g., fluids, reagents, etc.) are aqueous, organic or inorganic. Additionally, preparation methods can affect the shape and size of the microcapsule. For example a capsule's shape, (e.g., spherical, ellipsoidal, etc.), may depend on the shape of the droplet in the precursor liquid which may be determined by the viscosity and surface tension of the core liquid, direction of flow of the emulsion, the choice of surfactants used in droplet stabilization, as well as physical confinement such as preparations made in a microchannel or capillary of a particular size (e.g., a size requiring distortion of the microcapsule in order for the microcapsule to fit within the microchannel or capillary.

Microcapsules may be prepared through emulsification polymerization, a process in which monomer units at an aqueous/organic interface in an emulsion polymerize to form a shell. Reagents are mixed with the aqueous phase of the biphasic mixture. Vigorous shaking, or sonication of the mixture, creates droplets containing reagents, which are encased by a polymeric shell.

In some cases, microcapsules may be prepared through layer-by-layer assembly, a process in which negatively and positively charged polyelectrolytes are deposited onto particles such as metal oxide cores. Electrostatic interactions between polyelectrolytes create a polymeric shell around the core. The core can be subsequently removed via addition of acid, resulting in a semi-permeable hollow sphere which can be loaded with various reagents.

In still further cases, microcapsules may be prepared through coacervation, a process in which two oppositely charged polymers in aqueous solution become entangled to form a neutralized polymer shell wall. One polymer may be contained within an oil phase, while the other, of opposite charge is contained in an aqueous phase. This aqueous phase may contain reagents to be encapsulated. The attraction of one polymer for another can result in the formation of coacervates. In some embodiments, gelatin and gum Arabic are components of this preparative method.

Microcapsules also may be prepared through internal phase separation, a process in which a polymer is dissolved in a solvent mixture containing volatile and nonvolatile solvents. Droplets of the resultant solution are suspended in an aqueous layer, which is stabilized by continual agitation and the use of surfactants. This phase may contain reagents to be encapsulated. When the volatile solvent evaporates, the polymers coalesce to form a shell wall. In some cases, polymers such as polystyrene, poly(methyl methacrylate) and poly(tetrahydrofuran) are used to form shell walls.

Microcapsules also may be prepared through flow focusing methods, a process in which a microcapillary device is used to generate double emulsions containing a single internal droplet encased in a middle fluid which is then dispersed to an outer fluid. The inner droplet may contain reagents to be encapsulated. The middle fluid becomes the shell wall, which can be formed via cross-linking reactions.

B. Microcapsule Composition

Microcapsules may comprise a variety of materials with a wide range of chemical characteristics. Generally, the microcapsules comprise materials with the ability to form microcapsules of a desired shape and size and that are compatible with the reagents to be stored in the microcapsules.

Microcapsules may comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly (vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Often, materials for the microcapsules, particularly the shells of microcapsules, may enable the microcapsule to be disrupted with an applied stimulus. For example, a microcapsule may be prepared from heat sensitive polymers and/or may comprise one or more shells comprising such heat-sensitive polymers. The heat-sensitive polymer may be stable under conditions used for storage or loading. Upon exposure to heat, the heat-sensitive polymer components may undergo depolymerization, resulting in disruption to the integrity of the shell and release of the inner materials of the microcapsule (and/or of the inner microcapsules) to the outside environment (e.g., the interior of a microwell). Exemplary heat-sensitive polymers may include, but are not limited to NIPAAm or PNIPAM hydrogel. The microcapsules may also comprise one or more types of oil. Exemplary oils include but are not limited to hydrocarbon oils, fluorinated oils, fluorocarbon oils, silicone oils, mineral oils, vegetable oils, and any other suitable oil.

The microcapsules may also comprise a surfactant, such as an emulsifying surfactant. Exemplary surfactants include, but are not limited to, cationic surfactants, non-ionic surfactants, anionic surfactants, hydrocarbon surfactants or fluorosurfactants. The surfactant may increase the stability of one or more components of the microcapsule, such as an inner compartment that comprises an oil.

Additionally, the microcapsules may comprise an inner material that is miscible with materials external to the capsule. For example, the inner material may be an aqueous fluid and the sample within the microwell may also be in an aqueous fluid. In other examples, the microcapsule may comprise powders or nanoparticles that are miscible with an aqueous fluid. For example, the microcapsule may comprise such powders or nanoparticles in an inner compartment. Upon disruption of the microcapsule, such powders or nanoparticles are released into the external environment (e.g., interior of microwell) and may mix with an aqueous fluid (e.g., an aqueous sample fluid).

Additionally, the microcapsule may comprise a material that is immiscible with the surrounding environment (e.g., interior of microwell, sample fluid). In such cases, when the inner emulsion is released to the surrounding environment, the phase separation between the inner and outer components may promote mixing, such as mixing of the inner components with the surrounding fluid. In some cases, when a microcapsule is triggered to release its contents, a pressure or force is also released that promotes mixing of internal and external components.

The microcapsules may also comprise a polymer within the interior of the capsule. In some instances this polymer may be a porous polymer bead that may entrap reagents or combinations of reagents. In other instances, this polymer may be a bead that has been previously swollen to create a gel. Examples of polymer based gels that may be used as inner emulsions of capsules may include, but are not limited to sodium alginate gel, or poly acrylamide gel swelled with oligonucleotide bar codes or the like.

In some cases, a microcapsule may be a gel bead comprising any of the polymer based gels described herein. Gel bead microcapsules may be generated, for example, by encapsulating one or more polymeric precursors into droplets. Upon exposure of the polymeric precursors to an accelerator (e.g., tetramethylethylenediamine (TEMED)), a gel bead may be generated.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some cases, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some cases, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte.

A gel bead or any other type of microcapsule described herein may contain varied numbers of reagents. The density of a reagent per microcapsule may vary depending on the particular microcapsule utilized and the particular reagent. For example, a microcapsule or gel bead may comprise at least about 1; 10; 100; 1,000; 10,000; 100,000; 1,000,000; 5,000,000; 10,000,000; 50,000,000; 100,000,000; 500,000,000; or 1,000,000,000 oligonucleotide barcodes per microcapsule or gel bead. A gel bead may comprise identical oligonucleotide barcodes or may comprise differing oligonucleotide barcodes.

In other example, the microcapsule may comprise one or more materials that create a net neutral, negative or positive charge on the outer shell wall of the capsule. In some instances, the charge of a capsule may aid in preventing or promoting aggregation or clustering of particles, or adherence or repulsion to parts of the device.

In addition, the microcapsule may comprise one or more materials that cause the outer shell wall of the capsule to be hydrophilic or hydrophobic. A hydrophilic material that may be used for capsule shell walls may be poly(N-isopropylacrylamide). A hydrophobic material that may be used for capsule shell walls may be polystyrene. In certain instances, a hydrophilic shell wall may aid in wicking of the capsule into wells comprising aqueous fluid.

C. Microcapsule Size and Shape

A microcapsule may be any of a number of sizes or shapes. In some cases, the shape of the microcapsule may be spherical, ellipsoidal, cylindrical, hexagonal or any other symmetrical or non-symmetrical shape. Any cross-section of the microcapsule may also be of any appropriate shape, include but not limited to: circular, oblong, square, rectangular, hexagonal, or other symmetrical or non-symmetrical shape. In some cases, the microcapsule may be of a specific shape that complements an opening (e.g., surface of a microwell) of the device. For example, the microcapsule may be spherical and the opening of a microwell of the device may be circular.

The microcapsules may be of uniform size (e.g., all of the microcapsules are the same size) or heterogeneous size (e.g., some of the microcapsules are of different sizes). A dimension (e.g., diameter, cross-section, side, etc.) of a microcapsule may be at least about 0.001 µm, .01 µm, 0.1 µm, 0.5 µm, 1 µm, 5 µm, 10 µm, 50 µm, 100 µm, 200 µm, 300 µm, 400 µm, 500 µm, 600 µm, 700 µm, 800 µm, 900 µm or 1 nm. In some cases, the microcapsule comprises a microwell that is at most about 0.001 µm, .0.01 µm, 0.1 µm, 0.5 µm, 1 µm, 5 µm, 10 µm, 50 µm, 100 µm, 200 µm, 300 µm, 400 µm, 500 µm, 600 µm, 700 µm, 800 µm, 900 µm or 1 nm.

In some cases, microcapsules are of a size and/or shape so as to allow a limited number of microcapsules to be deposited in individual partitions (e.g., microwells, droplets) of the microcapsule array. Microcapsules may have a specific size and/or shape such that exactly or no more than 1, 2, 3, 4, 5, 6, 7, 8, 9, or 10 capsules fit into an individual microwell; in some cases, on average 1, 2, 3, 4, 5, 6, 7, 8, 9, or 10 capsules fit into an individual microwell. In still further cases, at least 1, 2, 3, 4, 5, 6, 7, 8, 9, 10, 100, 500, or 1000 capsules fit into an individual microwell.

D. Reagents and Reagent Loading

The devices provided herein may comprise free reagents and/or reagents encapsulated into microcapsules. The reagents may be a variety of molecules, chemicals, particles, and elements suitable for sample preparation reactions of an analyte. For example, a microcapsule used in a sample preparation reaction for DNA sequencing of a target may comprise one or more of the following reagents: enzymes, restriction enzymes (e.g., multiple cutters), ligase, polymerase (e.g., polymerases that do and do not recognize dUTPs and/or uracil), fluorophores, oligonucleotide barcodes, buffers, deoxynucleotide triphosphates (dNTPs) (e.g.deoxyadenosine triphosphate (dATP), deoxycitidine triphosphate (dCTP), deoxyguanosine triphosphate (dGTP), deoxythymidine triphosphate (dTTP), deoxyuridine triphosphate (dUTP)), deoxynucleotide triphosphates (ddNTPs)

and the like. In another example, a microcapsule used in a sample preparation reaction for single cell analysis may comprise reagents such as one or more of the following reagents: lysis buffer, detergent, fluorophores, oligonucleotide barcodes, ligase, proteases, heat activatable proteases, protease or nuclease inhibitors, buffer, enzymes, antibodies, nanoparticles, and the like.

Exemplary reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, nucleic acid, antibodies, saccharides, lipid, oil, salt, ion, detergents, ionic detergents, non-ionic detergents, oligonucleotides, nucleotides, dNTPs, ddNTPs, deoxyribonucleic acid (DNA), ribonucleic acid (RNA), peptide nucleic acids, circular DNA (cDNA), double-stranded DNA (dsDNA), single-stranded DNA (ssDNA), plasmid DNA, cosmid DNA, chromosomal DNA, genomic DNA (gDNA), viral DNA, bacterial DNA, mtDNA (mitochondrial DNA), messenger RNA (mRNA), ribosomal RNA (rRNA), transfer RNA (tRNA), nRNA, short-interfering RNA (siRNA), small nuclear RNA (snRNA), small nucleolar RNA (snoRNA), small Cajul body specific RNA, (scaRNA), microRNA, double-stranded RNA (dsRNA), ribozyme, riboswitch and viral RNA, polymerase (e.g., polymerases that do and do not recognize dUTPs and/or uracil), ligase, restriction enzymes, proteases, nucleases, protease inhibitors, nuclease inhibitors, chelating agents, reducing agents (e.g., dithiotheritol (DTT), 2-tris(2-carboxyethyl) phosphine (TCEP)), oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds.

In some cases, a microcapsule comprises a set of reagents that have a similar attribute (e.g., a set of enzymes, a set of minerals, a set of oligonucleotides, a mixture of different bar-codes, a mixture of identical bar-codes). In other cases, a microcapsule comprises a heterogeneous mixture of reagents. In some cases, the heterogeneous mixture of reagents comprises all components necessary to perform a reaction. In some cases, such mixture comprises all components necessary to perform a reaction, except for 1, 2, 3, 4, 5, or more components necessary to perform a reaction. In some cases, such additional components are contained within a different microcapsule or within a solution within a partition (e.g., microwell) of the device.

Reagents may be pre-loaded into the device (e.g., prior to introduction of analyte) or post-loaded into the device. They may be loaded directly into the device; or, in some cases, the reagents are encapsulated into a microcapsule that is loaded into the device. In some cases, only microcapsules comprising reagents are introduced. In other cases, both free reagents and reagents encapsulated in microcapsules are loaded into the device, either sequentially or concurrently. In some cases, reagents are introduced to the device either before or after a particular step. For example, a lysis buffer reagent may be introduced to the device following partitioning of a cellular sample into multiple partitions (e.g., microwells, droplets) within the device. In some cases, reagents and/or microcapsules comprising reagents are introduced sequentially such that different reactions or operations occur at different steps. The reagents (or microcapsules) may be also loaded at steps interspersed with a reaction or operation step. For example, microcapsules comprising reagents for fragmenting molecules (e.g., nucleic acids) may be loaded into the device, followed by a fragmentation step, which may be followed by loading of microcapsules comprising reagents for ligating bar-codes (or other unique identifiers, e.g., antibodies) and subsequent ligation of the bar-codes to the fragmented molecules. Additional methods of loading reagents are described further herein in other sections.

E. Molecular 'Barcodes'

It may be desirable to retain the option of identifying and tracking individual molecules or analytes after or during sample preparation. In some cases, one or more unique molecular identifiers, sometimes known in the art as a 'molecular barcodes,' are used as sample preparation reagents. These molecules may comprise a variety of different forms such as oligonucleotide bar codes, antibodies or antibody fragments, fluorophores, nanoparticles, and other elements or combinations thereof. Depending upon the specific application, molecular barcodes may reversibly or irreversibly bind to the target analyte and allow for identification and/or quantification of individual analytes after recovery from a device after sample preparation.

A device of this disclosure may be applicable to nucleic acid sequencing, protein detection, single molecule analysis and other methods that require a) precise measurement of the presence and amount of a specific analyte b) multiplex reactions in which multiple analytes are pooled for analysis. A device of this disclosure may utilize the microwells of the microwell array or other type of partition (e.g., droplets) to physically partition target analytes. This physical partitioning allows for individual analytes to acquire one or more molecular barcodes. After sample preparation, individual analytes may be pooled or combined and extracted from a device for multiplex analysis. For most applications, multiplex analysis substantially decreases the cost of analysis as well as increases through-put of the process, such as in the case of the nucleic acid sequencing. Molecular barcodes may allow for the identification and quantification of individual molecules even after pooling of a plurality of analytes. For example, with respect to nucleic acid sequencing, molecular barcodes may permit the sequencing of individual nucleic acids, even after the pooling of a plurality of different nucleic acids.

Oligonucleotide barcodes, in some cases, may be particularly useful in nucleic acid sequencing. In general, an oligonucleotide barcode may comprise a unique sequence (e.g., a barcode sequence) that gives the oligonucleotide barcode its identifying functionality. The unique sequence may be random or non-random. Attachment of the barcode sequence to a nucleic acid of interest may associate the barcode sequence with the nucleic acid of interest. The barcode may then be used to identify the nucleic acid of interest during sequencing, even when other nucleic acids of interest (e.g., comprising different barcodes) are present. In cases where a nucleic acid of interest is fragmented prior to sequencing, an attached barcode may be used to identify fragments as belonging to the nucleic acid of interest during sequencing.

An oligonucleotide barcode may consist solely of a unique barcode sequence or may be included as part of an oligonucleotide of longer sequence length. Such an oligonucleotide may be an adaptor required for a particular sequencing chemistry and/or method. For example, such adaptors may include, in addition to an oligonucleotide barcode, immobilization sequence regions necessary to immobilize (e.g., via hybridization) the adaptor to a solid surface (e.g., solid surfaces in a sequencer flow cell channel); sequence regions required for the binding of sequencing primers; and/or a random sequence (e.g., a random N-mer) that may be useful, for example, in random amplification schemes. An adaptor can be attached to a nucleic acid to be sequenced, for example, by amplification, ligation, or any other method described herein.

Moreover, an oligonucleotide barcode, and/or a larger oligonucleotide comprising an oligonucleotide barcode may comprise natural nucleic acid bases and/or may comprise non-natural bases. For example, in cases where an oligonucleotide barcode or a larger oligonucleotide comprising an oligonucleotide barcode is DNA, the oligonucleotide may comprise the natural DNA bases adenine, guanine, cytosine, and thymine and/or may comprise non-natural bases such as uracil.

F. Microcapsule-Preparation for Microwell Loading

Following preparation, reagent loaded microcapsules may be loaded into a device using a variety of methods. Microcapsules, in some instances, may be loaded as 'dry capsules.' After preparation, capsules may be separated from a liquid phase using various techniques, including but not limited to differential centrifugation, evaporation of the liquid phase, chromatography, filtration and the like. 'Dry capsules' may be collected as a powder or particulate matter and then deposited into microwells of the microwell array. Loading 'dry capsules' may be a preferred method in instances in which loading of 'wet capsules,' leads to inefficiencies of loading such as empty wells and poor distribution of microcapsules across the microwell array.

Reagent-loaded microcapsules may also be loaded into a device when the microcapsules are within a liquid phase, and thereby loaded as 'wet capsules.' In some instances, microcapsules may be suspended in a volatile oil such that the oil can be removed or evaporated, leaving only the dry capsule in the well. Loading 'wet capsules' may be a preferred method in some instances in which loading of dry capsules leads to inefficiencies of loading, such as microcapsule clustering, aggregation and poor distribution of microcapsules across the microwell array. Additional methods of loading reagents and microcapsules are described in other sections of this disclosure.

The microcapsules also may have a particular density. In some cases, the microcapsules are less dense than an aqueous fluid (e.g., water); in some cases, the microcapsules are denser than an aqueous fluid (e.g., water). In some cases, the microcapsules are less dense than a non-aqueous fluid (e.g., oil); in some cases, the microcapsules are denser than a non-aqueous fluid (e.g., oil). Microcapsules may comprise a density at least about 0.05 g/cm$^3$, 0.1 cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, microcapsule densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the microcapsule in any particular fluid (e.g., aqueous, water, oil, etc.)

III. Microwell Array

A. Structure/Features

A device of this disclosure may be a microwell array comprising a solid plate containing a plurality of holes, cavities or microwells in which microcapsules and/or analytes are deposited. Generally, a fluidic sample (or analyte) is introduced into the device (e.g., through an inlet) and then travels through a flow channel which distributes the sample into multiple microwells. In some cases, additional fluid is introduced into the device as well. The microwells may comprise microcapsules when the sample is introduced; or, in some cases, the microcapsules are introduced into the microwells following introduction of the sample.

Figure 2A:
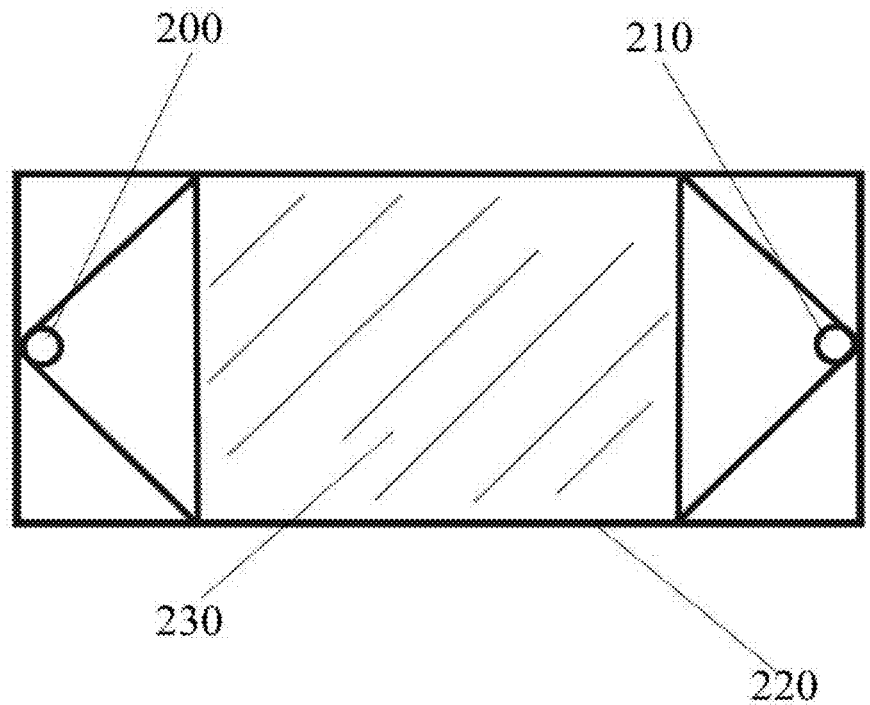
FIG. 2A is a schematic illustration of a top down view of an exemplary microcapsule array.
Figure 2B:
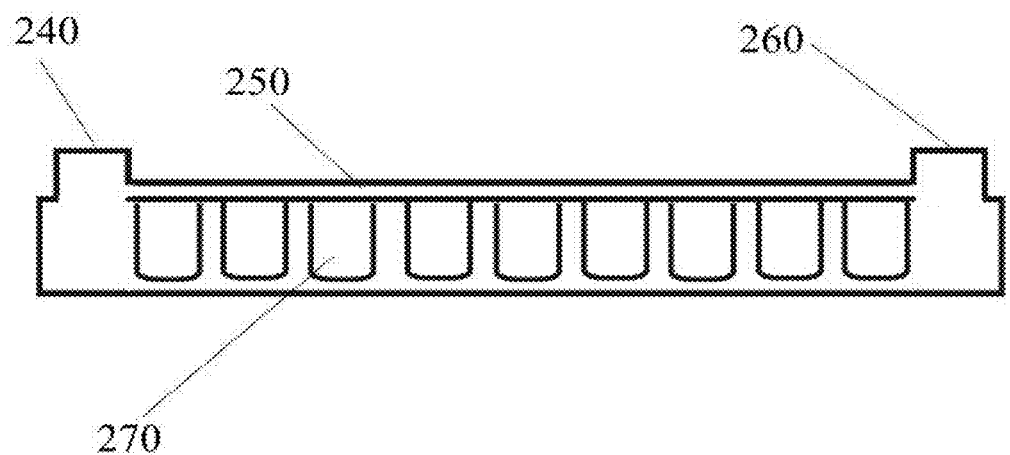
FIG. 2B is a schematic illustration of an exemplary side view of a microcapsule array.

FIG. 2A depicts a prototype microwell array; a sideview is depicted in FIG. 2B. The microwell array may include a plate 220 that can be made of any suitable material commonly used in a chemical laboratory, including fused silica, soda lima glass, borosilicate glass, PMMA, sapphire, silicon, germanium, cyclic olefin copolymer and cyclic polymer, polyethylenes, polypropylenes, polyacrylates, polycarbonates, plastics, Topas, and other suitable substrates known in the art. The plate 220 may initially be a flat solid plate comprising a regular pattern of microwells 270. The microwells may be formed by drilling or chemical dissolution or any other suitable method of machining; however, plates with a desired hole pattern are preferably molded, e.g. by injection-molding, embossing, or using a suitable polymer, such as cyclic olefin copolymer.

The microwell array may comprise an inlet (200 and 240) and/or an outlet (210 and 260); in some cases, the microwell array comprises multiple inlets and/or outlets. A sample (or analyte) or microcapsules may be introduced to the device via the inlet. Solutions containing analytes, reagents and/or microcapsules may be manually applied to the inlet port 200 and 240 (or to a conduit attached to the inlet port) via a pipette. In some cases, a liquid handling device is used to introduce analytes, reagents, and/or microcapsules to the device. Exemplary liquid handling devices may rely on a pipetting robot, capillary action, or dipping into a fluid. In some cases, the inlet port is connected to a reservoir comprising microcapsules or analytes. The inlet port may be attached to a flow channel 250 that permits distribution of the analyte, sample, or microcapsules to the microwells in the device. In some cases, the inlet port may be used to introduce to the device a fluid (e.g., oil, aqueous) that does not contain microcapsules or analyte, such as a carrier fluid. The carrier fluid may be introduced via the inlet port before, during, or following the introduction of analyte and/or microcapsules. In cases where the device has multiple inlets, the same sample may be introduced via the multiple inlets, or each inlet may convey a different sample. In some cases, one inlet may convey a sample or analyte to the microwells, while a different inlet conveys free reagents and/or reagents encapsulated in microcapsules to the device. The device may have at least 1, 2, 3, 4, 5, 6, 7, 8, 9, or 10 inlets and/or outlets.

In some cases, solutions containing microcapsules and/or analytes may be pulled through the device via a vacuum manifold attached to the outlet port 210 and 260. Such manifold may apply a negative pressure to the device. In other cases, a positive pressure is used to move sample, analytes, and/or microcapsules through the device. The area, length, and width of surfaces of 230 according to this disclosure may be varied according to the requirements of the assay to be performed. Considerations may include, for example, ease of handling, limitations of the material(s) of which the surface is formed, requirements of detection or processing systems, requirements of deposition systems (e.g. microfluidic systems), and the like. The thickness may comprise a thickness of at least about 0.001 mm, 0 005 mm, 0.01 mm, 0 05 mm, 0 1 mm, 0 2 mm, 0 3 mm, 0 4 mm, 0 5 mm, 0 6 mm, 0 7 mm, 0 8 mm, 0 9 mm, 10 mm, 20 mm, 30 mm, 40 mm, 50 mm, 60 mm, 70 mm, 8.0 mm, 90 mm, 10 0 mm, 11 mm, 12 mm, 13 mm, 14 mm, or 15 mm. In other cases, microcapsule thickness may be at most 0.001 mm, 0 005 mm, 0.01 mm, 0 05 mm, 0 1 mm, 0 2 mm, 0 3 mm, 0 4 mm, 0 5 mm, 0 6 mm, 0 7 mm, 0 8 mm, 0 9 mm, 10 mm, 20 mm, 30 mm, 40 mm, 50 mm, 60 mm, 70 mm, 8.0 mm, 90 mm, 10 0 mm, 11 mm, 12 mm, 13 mm, 14 mm, or 15 mm.

The microwells 270 can be any shape and size suitable for the assay performed. The cross-section of the microwells may have a cross-sectional dimension that is circular, rectangular, square, hexagonal, or other symmetric or non-symmetric shape. In some cases, the shape of the microwell may be cylindrical, cubic, conical, frustoconical, hexagonal or other symmetric or non-symmetric shape. The diameter of the microwells 270 may be determined by the size of the wells desired and the available surface area of the plate itself. Exemplary microwells comprise diameters of at least 0.01 µm, 0.1 µm, 0.2 µm, 0.3 µm, 0.4 µm, 0.5 µm, 1 µm, 10 µm, 25 µm, 50 µm, 75 µm, 100 µm, 200 µm, 300 µm, 400 µm, 500 µm, 600 µm, 700 µm, 800 µm, 900 µm, 1.0 mm. In other cases, microwell diameters may comprise at most 0.01 µm, 0.1 µm, 0.2 µm, 0.3 µm, 0.4 µm, 0.5 µm, 1 µm, 10 µm, 25 µm, 50 µm, 75 µm, 100 µm, 200 µm, 300 µm, 400 µm, 500 µm, 600 µm, 700 µm, 800 µm, 900 µm or 1.0 mm.

The capacity (or volume) of each well can be a measure of the height of the well (the thickness of the plate) and the effective diameter of each well. The capacity of an individual well may be selected from a wide range of volumes. In some cases, the device may comprise a well (or microwell) with a capacity of at least 0.001 fL, .01 fL, 0.1 fL, 0.5 fL, 1 fL, 5 fL, 10 fL, 50 fL, 100 fL, 200 fL, 300 fL, 400 fL, 500 fL, 600 fL, 700 fL, 800 fL, 900 fL, 1 pL, 5 pL, 10 pL, 50 pL, 100 pL, 200 pL, 300 pL, 400 pL, 500 pL, 600 pL, 700 pL, 800 pL, 900 pL, 1 nL, 5 nL, 10 nL, 50 nL, 100 nL, 200 nL, 300 nL, 400 nL, 500 nL, 1 uL, 50 uL, or 100 uL. In other cases, the microcapsule comprises a microwell that is less than 0.001 fL, .01 fL, 0.1 fL, 0.5 L, 5 fL, 10 fL, 50 fL, 100 fL, 200 fL, 300 fL, 400 fL, 500 fL, 600 fL, 700 fL, 800 fL, 900 fL, 1 pL, 5 pL, 10 pL, 50 pL, 100 pL, 200 pL, 300 pL, 400 pL, 500 pL, 600 pL, 700 pL, 800 pL, 900 pL, 1 nL, 5 nL, 10 nL, 50 nL, 100 nL, 200 nL, 300 nL, 400 nL, 500 nL, 1 uL, 50 uL, or 100 uL.

There may be variability in the volume of fluid in different microwells in the array. More specifically, the volume of different microwells may vary by at least (or at most) plus or minus 1%, 2%, 3%, 4%, 5%, 10%, 20%, 30%, 40%, 50%, 60%, 70%, 80%, 90%, 100%, 200%, 300%, 400%, 500%, or 1000% across a set of microwells. For example, a microwell may comprise a volume of fluid that is at most 80% of the fluid volume within a second microwell.

Based on the dimension of individual microwells and the size of the plate, the microwell array may comprise a range of well densities. In some examples, a plurality of microwells may have a density of at least about 2,500 wells/cm$^2$, at least about 1,000 wells/cm$^2$. in some cases, the plurality of wells may have a density of at least 10 wells/cm$^2$. In other cases, the well density may comprise at least 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In other cases, the well density may be less than 100000 wells/cm$^2$, 10000 wells/cm$^2$, 5000 wells/cm$^2$, 1000 wells/cm$^2$, 500 wells/cm$^2$, or 100 wells/cm$^2$.

In some cases, the interior surface of the microwells comprises a hydrophilic material that preferably accommodates an aqueous sample; in some cases, the region between the microwells is composed of a hydrophobic material that may preferentially attract a hydrophobic sealing fluid described herein.

Figure 3:
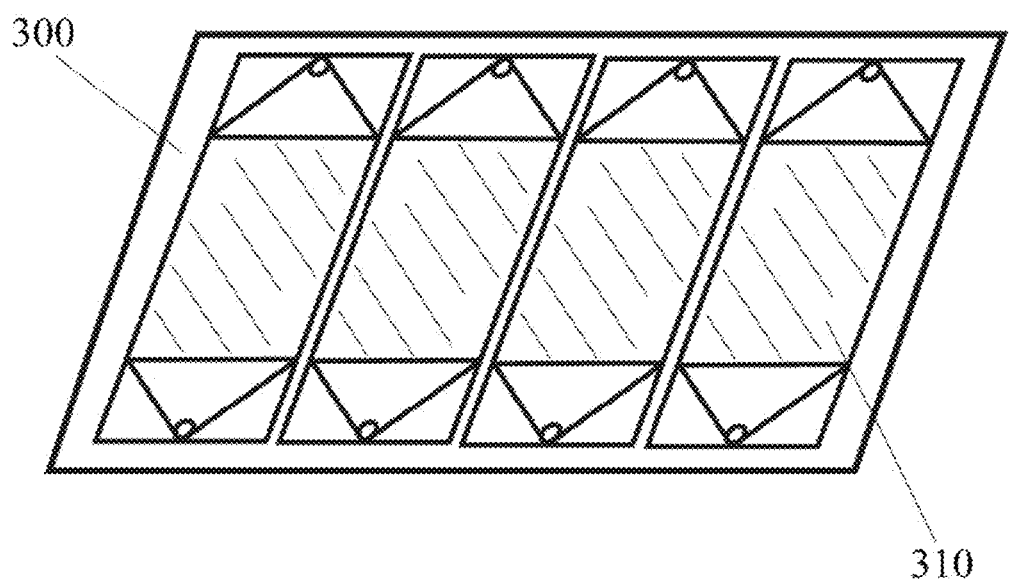
FIG. 3 is a schematic illustration of a multi-microcapsule array configuration on a 96-well plate holder.

Multiple microwell arrays, e.g., FIG. 2B may be arranged within a single device. FIG. 3, 300. For example, discrete microwell array slides may be arrayed in parallel on a plate holder. In some cases, at least 1, 2, 3, 4, 5, 6, 7, 8, 9, 10, 25, 50 or 100 microwell arrays are arrayed in parallel. In other cases, at most 100, 50, 25, 10, 9, 8, 7, 6, 5, 4, 3, 2 or 1 devices are arrayed in parallel. The microwell arrays within a common device may be manipulated simultaneously or sequentially. For example, arrayed devices may be loaded with samples or capsules simultaneously or sequentially.

B. Microwell Array Fluids

The microwell array may comprise any of a number of different fluids including aqueous, non-aqueous, oils, and organic solvents, such as alcohols. In some cases, the fluid is used to carry a component, e.g., reagent, microcapsule, or analyte, to a target location such as microwells, output port, etc. In other cases, the fluid is used to flush the system. In still other cases, the fluid may be used to seal the microwells.

Any fluid or buffer that is physiologically compatible with the analytes (e.g., cells, molecules) or reagents used in the device may be used. In some cases, the fluid is aqueous (buffered or not buffered). For example, a sample comprising a population of cells suspended in a buffered aqueous solution may be introduced into the microwell array, allowed to flow through the device, and distributed to the microwells. In other cases, the fluid passing through the device is nonaqueous (e.g., oil). Exemplary non-aqueous fluids include but are not limited to: oils, non-polar solvent, hydrocarbon oil, decane (e.g., tetradecane or hexadecane), fluorocarbon oil, fluorinated oil, silicone oil, mineral oil, or other oil.

Often, the microcapsules are suspended in a fluid that is compatible with the components of the shell of the microcapsule. Fluids including but not limited to water, alcohols, hydrocarbon oils or fluorocarbon oils are particularly useful fluids for suspending and flowing microcapsules through the microarray device.

C. Further Partitioning and Sealing

After the analyte, free reagents, and/or microcapsules are loaded into the device and distributed to the microwells, a sealing fluid may be used to further partition or isolate them within the microwells. The sealing fluid may also be used to seal the individual wells. The sealing fluid may be introduced through the same inlet port that was used to introduce the analyte, reagents and/or microcapsules. But in some cases, the sealing fluid is introduced to the device by a separate inlet port, or through multiple separate inlet ports.

Often, the sealing fluid is a non-aqueous fluid (e.g., oil). When the sealing fluid flows through the microwell array device, it may displace excess aqueous solution (e.g., solution comprising analytes, free reagents and/or microcapsules) from individual microwells, thereby potentially removing aqueous bridges between adjacent microwells. The wells themselves, as described herein, may comprise a hydrophilic material that enables wicking of the aqueous fluids (e.g., sample fluid, microcapsule fluid) into individual wells. In some cases, regions external to the wells comprise hydrophobic material, again to encourage the positioning of the aqueous fluid into the interior of the microwells.

The sealing fluid may either remain in the device or be removed. The sealing fluid may be removed, e.g., by flowing through the outlet port. In other cases, the sealing oil may comprise a volatile oil that can be removed by the application of heat. Once the sealing fluid is removed, analytes, free reagents and/or microcapsules may be physically partitioned from one another in the microwells.

A fluid may be selected such that its density is equal to, greater than or less than the density of the microcapsules. For example, the microcapsules may be denser than the sealing oil and/or aqueous fluid of the sample and reagents, thereby enabling the microcapsules to remain in the microwells as the sealing oil flows through the device. In another example, the capsules may be less dense than the aqueous fluid of the sample or the fluid that the microcapsules are suspended in, as described herein, thereby facilitating movement and distribution of the capsules across the plurality of microwells in a device.

In the case of microcapsules comprising paramagnetic material, a magnetic field may be used to load or direct the capsules into the microwells. A magnetic field may also be used to retain such microcapsules within the wells while the wells are being filled with sample, reagent, and/or sealing fluids. The magnetic field may also be used to remove capsule shells from the wells, particularly following rupture of the capsules.

In some cases, the sealing fluid may remain in the microwells when operations or reactions are conducted therein. The presence of the sealing fluid may act to further partition, isolate, or seal the individual microwells. In other cases, the sealing fluid may act as a carrier for the microcapsules. For example, sealing fluid comprising microcapsules may be introduced to the device to facilitate distribution of the microcapsules to the individual microwells. For such applications, the sealing fluid may be denser than the microcapsules in order to encourage more even distribution of the microcapsules to the microwells. Upon application of a stimulus, the microcapsules within the sealing fluid may release reagents to the microwell. In some cases, the sealing fluid may comprise a chemical or other agent capable of traveling from the sealing fluid to a well (e.g., by leaching or other mechanism) and triggering capsule rupture, where the capsule is present within the microwell or within the sealing fluid.

Methods other than those involving sealing fluids may also be used to seal the microwells following the loading of the analyte, free reagents, and/or microcapsules. For example, the microwells may be sealed with a laminate, tape, plastic cover, oils, waxes, or other suitable material to create an enclosed reaction chamber. The sealants described herein may protect the contents of the microwells from evaporation or other unintended consequences of the reactions or operations. Prevention of evaporation may be particularly necessary when heat is applied to the device, e.g., when heat is applied to stimulate microcapsule release.

In some cases, the laminate seal may also allow recovery of contents from individual wells. In this case, a single well of interest may be unsealed (e.g., by removal of the laminate seal) at a given time in order to enable further analysis of an analyte such as by MALDI mass spectrometry. Such applications may be useful in a number of settings, including high-throughput drug screening.

III. Loading Step(s)

As described herein, analytes, free reagents, and/or microcapsules may be loaded into the present device in any appropriate manner or order. The loading may be random or non-random. In some cases, a precise number of analytes and/or microcapsules are loaded into each individual microwell. In some cases, a precise number of analytes and/or microcapsules are loaded into a particular subset of microwells in the plate. In still other cases, an average number of analytes and/or micrcocapsules are loaded into each individual microwell. Furthermore, as described herein, in some cases, "dry" microcapsules are loaded into the device, while in other cases "wet" microcapsules are loaded into the device. In some cases, a combination of "dry" and "wet" microcapsules and/or reagents are loaded into the device, either simultaneously or sequentially.

As mentioned herein, the loading of the device may occur in any order and may occur in multiple stages. In some cases, the microcapsules are pre-loaded into the device, prior to the loading of the analyte. In other cases, the microcapsules and analyte are loaded concurrently. In still other cases, the analytes are loaded before the microcapsules are loaded.

The microcapsules and/or analytes may be loaded in multiple stages or multiple times. For example, microcapsules may be loaded into the device both prior to and after analytes are loaded into the device. The microcapsules that are pre-loaded (e.g., loaded prior to the analyte introduction) may comprise the same reagents as the microcapsules loaded after the analyte introduction. In other cases, the pre-loaded microcapsules contain reagents that are different from the reagents within the microcapsules loaded after analyte introduction. In some cases, at least 1, 2, 3, 4, 5, 6, 7, 8, 9, 10, 15, or 20 different sets of microcapsules are loaded onto the device. In some cases, the different sets of microcapsules are loaded sequentially; or, different sets of microcapsules may also be loaded simultaneously. Similarly, multiple sets of analytes can be loaded into the device. In some cases, at least 1, 2, 3, 4, 5, 6, 7, 8, 9, 10, 15, or 20 different sets of analytes are loaded onto the device. In some cases, the different sets of analytes are loaded sequentially; or, different sets of analytes may also be loaded simultaneously.

This disclosure provides devices comprising certain numbers of microcapsules and/or analytes loaded per well. In some cases, at most 1, 2, 3, 4, 5, 6, 7, 8, 9, 10, 15, 20, 30, 40, 50, 75, or 100 microcapsules and/or analytes are loaded into each individual microwell. In some cases, at least 1, 2, 3, 4, 5, 6, 7, 8, 9, 10, 15, 20, 30, 40, 50, 75, or 100 microcapsules and/or analytes are loaded into each individual microwell. In some cases, on average, at most 1, 2, 3, 4, 5, 6, 7, 8, 9, 10, 15, 20, 30, 40, 50, 75, or 100 microcapsules and/or analytes are loaded into each individual microwell. In other cases, on average, at least 1, 2, 3, 4, 5, 6, 7, 8, 9, 10, 15, 20, 30, 40, 50, 75, or 100 microcapsules and/or analytes are loaded into each individual microwell. In some cases, about 1, 2, 3, 4, 5, 6, 7, 8, 9, 10, 15, 20, 30, 40, 50, 75, or 100 microcapsules and/or analytes are loaded into each individual microwell.

Analytes and/or microcapsules may be applied in a quantity that allows a desired number of analytes to be deposited into an individual microwell. For example, terminal dilution of analytes, such as cells, may achieve the loading of one cell per one microwell or any desired number of analytes per microwell. In some cases, a Poisson distribution is used to direct or predict the final concentration of analytes or microcapsules per well.

The microcapsules may be loaded into the microarray device in a particular pattern. For example, certain sections of the device may comprise microcapsules containing a particular reagent (e.g., unique bar-code, enzyme, antibody, antibody subclass, etc.), while other sections of the device may comprise microcapsules containing a different reagent (e.g., a different bar-code, different enzyme, different antibody different antibody subclass, etc.). In some cases, the microcapsules in one section of the array may contain control reagents. For example, they may contain positive controls that include a control analyte and necessary materials for a reaction. Or, in some cases, the microcapsules contain negative control reagents such as deactivated enzyme, or a synthetic oligonucleotide sequence that is resistant to fragmentation. In some cases, negative control reagents may control for the specificity of the sample preparation reaction etc. In other cases, the negative control microcapsules may comprise the same reagents present in other microcapsules except that the negative control microcapsule may lack a certain reagent (e.g., lysis buffer, polymerase, etc.).

The analytes/sample also may be loaded into the microarray device in a particular pattern. For example, certain sections of the device may comprise particular analytes, such as control analytes or analytes deriving from a particular source. This may be used in combination with specific loading of bar codes into known well locations. This feature may allow mapping of specific locations on the array to sequence data, thereby reducing the number of bar codes to be used for labeling reactions.

In cases where a partition is a droplet, an analyte and reagents may be combined within the droplet with the aid of a microfluidic device. For example, a droplet may be generated that comprises a gel bead (e.g., comprising an oligonucleotide barcode) a nucleic acid analyte, and any other desired reagents. The gel bead, nucleic acid analyte, and reagents in an aqueous phase may be combined at a junction of two or more channels of a microfluidic device. At a second junction of two or more channels of the microfluidic device, a droplet comprising the resulting mixture may be generated by contacting the aqueous mixture of reagents, gel bead, and nucleic acid analyte with an oil continuous phase.

IV. Microcapsule Stimuli

Various different stimuli may be used to trigger release of reagents from the microcapsules, or from internal compartments therein. In some cases, a microcapsule is degradable. Generally, the trigger may cause disruption or degradation of the shell or membrane enveloping the microcapsule, disruption or degradation of the interior of a microcapsule, and/or disruption or degradation of any chemical bonds that immobilize a reagent to the microcapsule. Exemplary triggers include but are not limited to: chemical triggers, bulk changes, biological triggers, light triggers, thermal triggers, magnetic triggers, and any combination thereof. See, e.g., Esser-Kahn et al., (2011) *Macromolecules* 44: 5539-5553; Wang et al., (2009) *ChemPhysChem* 10:2405-2409;

A. Chemical Stimuli and Bulk Changes

Numerous chemical triggers may be used to trigger the disruption or degradation of the microcapsules. Examples of these chemical changes may include, but are not limited to pH-mediated changes to the shell wall, disintegration of the shell wall via chemical cleavage of crosslink bonds, triggered depolymerization of the shell wall, and shell wall switching reactions. Bulk changes may also be used to trigger disruption of the microcapsules.

A change in pH of the solution, particularly a decrease in pH, may trigger disruption via a number of different mechanisms. The addition of acid may cause degradation or disassembly of the shell wall through a variety of mechanisms. Addition of protons may disassemble cross-linking of polymers in the shell wall, disrupt ionic or hydrogen bonds in the shell wall, or create nanopores in the shell wall to allow the inner contents to leak through to the exterior. In some examples, the microcapsule comprises acid-degradable chemical cross-linkers such a ketals. A decrease in pH, particular to a pH lower than 5, may induce the ketal to convert to a ketone and two alcohols and facilitate disruption of the microcapsule. In other examples, the microcapsules may comprise one or more polyelectrolytes (e.g., PAA, PAAm, PSS, etc.) that are pH sensitive. A decrease in pH may disrupt the ionic- or hydrogen-bonding interactions of such microcapsules, or create nanopores therein. In some cases, microcapsules comprising polyelectrolytes comprise a charged, gel-based core that expands and contracts upon a change of pH.

Removal of cross-linkers (e.g., disulfide bonds) within the microcapsules can also be accomplished through a number of mechanisms. In some examples, various chemicals can be added to a solution of microcapsules that induce either oxidation, reduction or other chemical changes to polymer components of the shell wall. In some cases, a reducing agent, such as beta-mercaptoethanol, dithiotheritol (DTT), or 2-tris(2-carboxyethyl) phosphine (TCEP), is added such that disulfide bonds in a microcapsule shell wall are disrupted. In addition, enzymes may be added to cleave peptide bonds within the microcapsules, thereby resulting in cleavage of shell wall cross linkers.

Depolymerization can also be used to disrupt the microcapsules. A chemical trigger may be added to facilitate the removal of a protecting head group. For example, the trigger may cause removal of a head group of a carbonate ester or carbamate within a polymer, which in turn causes depolymerization and release of reagents from the inside of the capsule.

Shell wall switching reactions may be due to any structural change to the porosity of the shell wall. The porosity of a shell wall may be modified, for example, by the addition of azo dyes or viologen derivatives. Addition of energy (e.g., electricity, light) may also be used to stimulate a change in porosity.

In yet another example, a chemical trigger may comprise an osmotic trigger, whereby a change in ion or solute concentration of microcapsule solution induces swelling of the capsule. Swelling may cause a buildup of internal pressure such that the capsule ruptures to release its contents.

It is also known in the art that bulk or physical changes to the microcapsule through various stimuli also offer many advantages in designing capsules to release reagents. Bulk or physical changes occur on a macroscopic scale, in which capsule rupture is the result of mechano-physical forces induced by a stimulus. These processes may include, but are not limited to pressure induced rupture, shell wall melting, or changes in the porosity of the shell wall.

B. Biological Stimuli

Biological stimuli may also be used to trigger disruption or degradation of microcapsules. Generally, biological triggers resemble chemical triggers, but many examples use biomolecules, or molecules commonly found in living systems such as enzymes, peptides, saccharides, fatty acids, nucleic acids and the like. For example, microcapsules may comprise polymers with peptide cross-links that are sensitive to cleavage by specific proteases. More specifically, one example may comprise a microcapsule comprising GFLGK peptide cross links Upon addition of a biological trigger such as the protease Cathepsin B, the peptide cross links of the shell well are cleaved and the contents of the capsule are released. In other cases, the proteases may be heat-activated. In another example, microcapsules comprise a shell wall comprising cellulose. Addition of the hydrolytic enzyme chitosan serves as biologic trigger for cleavage of cellulosic bonds, depolymerization of the shell wall, and release of its inner contents.

C. Thermal Stimuli

The microcapsules may also be induced to release their contents upon the application of a thermal stimulus. A change in temperature can cause a variety changes to the microcapsule. A change in heat may cause melting of a microcapsule such that the shell wall disintegrates. In other cases, the heat may increase the internal pressure of the inner components of the capsule such that the capsule ruptures or explodes. In still other cases, the heat may transform the capsule into a shrunken dehydrated state. The heat may also act upon heat-sensitive polymers within the shell of a microcapsule to cause disruption of the microcapsule.

In one example, a microcapsule comprises a thermosensitive hydrogel shell encapsulating one or more emulsified reagent particles. Upon the application of heat, such as above 35 C., the hydrogel material of the outer shell wall shrinks. The sudden shrinkage of the shell ruptures the capsule and allows the reagents of the inside of the capsule to squirt out in the sample preparation solution in the microwell.

In some cases, the shell wall may comprise a diblock polymer, or a mixture of two polymers, with different heat sensitivities. One polymer may be particularly likely to shrink after the application of heat, while the other is more heat-stable. When heat is applied to such shell wall, the heat-sensitive polymer may shrink, while the other remains intact, causing a pore to form. In still other cases, a shell wall may comprise magnetic nanoparticles. Exposure to a magnetic field may cause the generation of heat, leading to rupture of the microcapsule.

D. Magnetic Stimuli

Inclusion of magnetic nanoparticles to the shell wall of microcapsules may allow triggered rupture of the capsules as well as guide the particles in an array. A device of this disclosure may comprise magnetic particles for either purpose. In one example, incorporation of Fe3O4 nanoparticles into polyelectrolyte containing capsules triggers rupture in the presence of an oscillating magnetic field stimulus.

E. Electrical and Light Stimuli

A microcapsule may also be disrupted or degraded as the result of electrical stimulation. Similar to magnetic particles described in the previous section, electrically sensitive particles can allow for both triggered rupture of the capsules as well as other functions such as alignment in an electric field, electrical conductivity or redox reactions. In one example, microcapsules containing electrically sensitive material are aligned in an electric field such that release of inner reagents can be controlled. In other examples, electrical fields may induce redox reactions within the shell wall itself that may increase porosity.

A light stimulus may also be used to disrupt the microcapsules. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with SiO2/TiO2 may result in disintegration of the capsule wall. In yet another example, photo switchable materials such as azobenzene groups may be incorporated in the shell wall. Upon the application of UV or visible light, chemicals such as these undergo a reversible cis-to-trans isomerization upon absorption of photons. In this aspect, incorporation of photo switches result in a shell wall that may disintegrate or become more porous upon the application of a light trigger.

F. Application of Stimuli

A device of this disclosure may be used in combination with any apparatus or device that provides such trigger or stimulus. For example, if the stimulus is thermal, a device may be used in combination with a heated or thermally controlled plate, which allows heating of the microwells and may induce the rupture of capsules. Any of a number of heat transfers may be used for thermal stimuli, including but not limited to applying heat by radiative heat transfer, convective heat transfer, or conductive heat transfer. In other cases, if the stimulus is a biological enzyme, the enzyme may be injected into a device such that it is deposited into each microwell. In another aspect, if the stimulus is a magnetic or electric field, a device may be used in combination with a magnetic or electric plate.

A chemical stimulus may be added to a partition and may exert its function at various times after contacting a chemical stimulus with a microcapsule. The speed at which a chemical stimulus exerts its effect may vary depending on, for example, the amount/concentration of a chemical stimulus contacted with a microcapsule and/or the particular chemical stimulus used. For example, a droplet may comprise a degradable gel bead (e.g., a gel bead comprising chemical cross-linkers, such as, for example, disulfide bonds). Upon droplet formation, a chemical stimulus (e.g., a reducing agent) may be included in the droplet with the gel bead. The chemical stimulus may degrade the gel bead immediately on contact with the gel bead, soon after (e.g., about 0, 0.5, 1, 2, 3, 4, 5, 6, 7, 8, 9, or 10 min) contact with the gel bead, or at a later time. In some cases, degradation of the gel bead may occur before, during, or after a further processing step, such as, for example, a thermal cycling step as described herein.

V. Sample Preparation, Reaction and Recovery

After application of the stimulus, rupturing of capsules and release of the reagents, the sample preparation reaction may proceed in a device. Reactions within a device may be incubated for various periods of times depending on the reagents used in the sample reactions. A device may also be used in combination with other devices that aid in the sample preparation reaction. For example, if PCR amplification is desired, a device may be used in combination with a PCR thermocycler. In some cases, a thermocycler may comprise a plurality of wells. In cases where partitions are droplets, the droplets may be entered into the wells of the thermocycler. In some cases, each well may comprise multiple droplets, such that when thermal cycling is initiated, multiple droplets are thermal cycled in each well. In another example, if the reaction requires agitation, a device may be used in combination with a shaking apparatus.

Following the completion of the sample preparation reaction, the analytes and products of the sample reactions may be recovered. In some cases, a device may utilize a method comprising the application of liquid or gas to flush out the contents of the individual microwells. In one example, the liquid comprises an immiscible carrier fluid that preferentially wets the microwell array material. It may also be immiscible with water so as to flush the reaction products out of the well. In another example, the liquid may be an aqueous fluid that can be used to flush out the samples out of the wells. After flushing of the contents of the microwells, the contents of the microwells are pooled for a variety of downstream analyses and applications.

VI. Applications

Figure 4A:
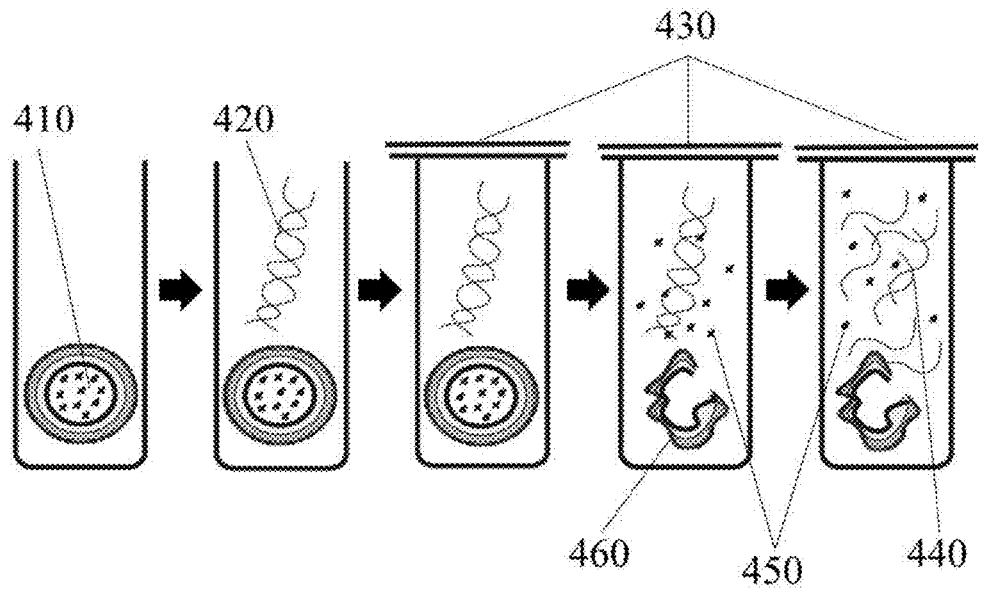
FIG. 4A is a schematic flow diagram representative of a reaction sequence in one microwell of a microwell capsule array.
Figure 4B:
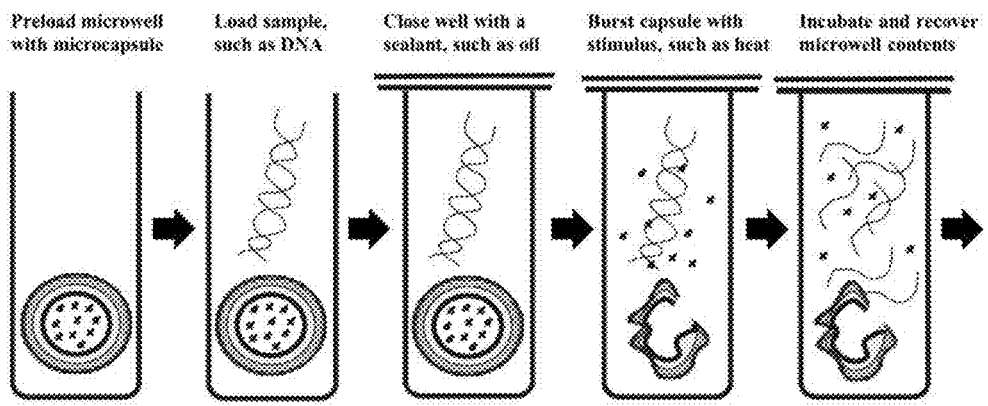
FIG. 4B is similar to 4A, except that it is annotated with examples of methods that can be performed at each step.

FIG. 4A provides a general flow of many of the methods of the present disclosure; and FIG. 4B provides a generally annotated version of 4A. One or more microcapsule(s) that contain reagents 410 may be pre-loaded into microwells, followed by addition of an analyte, which, in this particular Figure, is a nucleic acid analyte 420. The microwells may then be sealed 430 by any method, such as by application of a sealing fluid. The inlet and outlet ports may also be sealed, for example to prevent evaporation. Following these steps, a stimulus (e.g., heat, chemical, biological, etc.) may be applied to the microwells in order to disrupt the microcapsules 460 and trigger release of the reagents 450 to the interior of the microwell. Subsequently, an incubation step 440 may occur in order to enable the reagents perform a particular function such as lysis of cells, digestion of protein, fragmentation of high molecular weight nucleic acids, or ligation of oligonucleotide bar codes. Following the incubation step (which is optional), the contents of the microwells may be recovered either singly or in bulk.

A. Analytes

A device of this disclosure may have a wide variety of uses in the manipulation, preparation, identification and/or quantification of analytes. In some cases, the analyte is a cell or population of cells. The population of cells may be homogeneous (e.g., from a cell line, of the same cell type, from the same type of tissue, from the same organ, etc.) or heterogenous (mixture of different types of cells). The cells may be primary cells, cell lines, recombinant cells, primary cells, encapsulated cells, free cells, etc.

The analytes may also be molecules, including but not limited to: polypeptides, proteins, antibodies, enzymes, nucleic acids, saccharides, small molecules, drugs, and the like. Examples of nucleic acids include but are not limited to: DNA, RNA, dNTPs, ddNTPs, amplicons, synthetic nucleotides, synthetic polynucleotides, polynucleotides, oligonucleotides, peptide nucleic acids, cDNA, dsDNA, ssDNA, plasmid DNA, cosmid DNA, high Molecular Weight (MW) DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA (e.g., retroviral RNA).

In some cases, the analytes are pre-mixed with one or more additional materials, such as one or more reagents (e.g., ligase, protease, polymerase) prior to being loaded into the device. In some cases, the analytes are pre-mixed with microcapsules comprising one or more reagents prior to being loaded onto the device.

The samples may be derived from a variety of sources including human, mammal, non-human mammal, ape, monkey, chimpanzee, plant, reptilian, amphibian, avian, fungal, viral or bacterial sources. Samples such as cells, nucleic acids and proteins may also be obtained from a variety of clinical sources such as biopsies, aspirates, blood draws, urine samples, formalin fixed embedded tissues and the like.

A device of this disclosure may also enable the analytes to be tagged or tracked in order to permit subsequent identification of an origin of the analytes. This feature is in contrast with other methods that use pooled or multiplex reactions and that only provide measurements or analyses as an average of multiple samples. Here, the physical partitioning and assignment of a unique identifier to individual analytes allows acquisition of data from individual samples and is not limited to averages of samples.

In some examples, nucleic acids or other molecules derived from a single cell may share a common tag or identifier and therefore may be later identified as being derived from that cell. Similarly, all of the fragments from a single strand of nucleic acid may be tagged with the same identifier or tag, thereby permitting subsequent identification of fragments with similar phasing or linkage on the same strand. In other cases, gene expression products (e.g., mRNA, protein) from an individual cell may be tagged in order to quantify expression. In still other cases, the device can be used as a PCR amplification control. In such cases, multiple amplification products from a PCR reaction can be tagged with the same tag or identifier. If the products are later sequenced and demonstrate sequence differences, differences among products with the same identifier can then be attributed to PCR error.

The analytes may be loaded onto the device before, after, or during loading of the microcapsules and/or free reagents. In some cases, the analytes are encapsulated into microcapsules before loading into the microcapsule array. For example, nucleic acid analytes may be encapsulated into a microcapsule, which is then loaded onto the device and later triggered to release the analytes into an appropriate microwell.

Any analytes, such as DNA or cells, may be loaded in solution or as analytes encapsulated in a capsule. In some cases, homogeneous or heterogeneous populations of molecules (e.g., nucleic acids, proteins, etc.) are encapsulated into microcapsules and loaded onto the device. In some cases, homogeneous or heterogeneous populations of cells are encapsulated into microcapsules and loaded onto the device. The microcapsules may comprise a random or specified number of cells and/or molecules. For example, the microcapsules may comprise no more than 1, 2, 3, 4, 5, 6, 7, 8, 9, 10, 20, 30,40 ,50, 60, 70, 80, 90, 100, 500, 1000, 5000, or 10000 cells and/or molecules per microcapsule. In other examples, the microcapsules comprise at least 1, 2, 3, 4, 5, 6, 7, 8, 9, 10, 20, 30,40 ,50, 60, 70, 80, 90, 100, 500, 1000, 5000, or 10000 cells and/or molecules per microcapsule. Fluidic techniques and any other techniques may be used to encapsulate the cells and/or molecules into microcapsules.

Generally, the methods and compositions provided herein are useful for preparation of an analyte prior to a downstream application such as a sequencing reaction. Often, a sequencing method is classic Sanger sequencing. Sequencing methods may include, but are not limited to: high-throughput sequencing, pyrosequencing, sequencing-by-synthesis, single-molecule sequencing, nanopore sequencing, sequencing-by-ligation, sequencing-by-hybridization, RNA-Seq (Illumina), Digital Gene Expression (Helicos), Next generation sequencing, Single Molecule Sequencing by Synthesis (SMSS)(Helicos), massively-parallel sequencing, Clonal Single Molecule Array (Solexa), shotgun sequencing, Maxim-Gilbert sequencing, primer walking, and any other sequencing methods known in the art.

There are numerous examples of applications that may be conducted instead of, or in conjunction with, a sequencing reaction, including but not limited to: biochemical analyses, proteomics, immunoassays, profiling/fingerprinting of specific cell types, pharmaceutical screening, bait-capture experiments, protein-protein interaction screens and the like.

B. Assignment of Unique Identifiers to Analytes

The devices disclosed herein may be used in applications that involve the assignment of unique identifiers, or molecular bar codes, to analytes. Often, the unique identifier is a bar-code oligonucleotide that is used to tag the analytes; but, in some cases, different unique identifiers are used. For example, in some cases, the unique identifier is an antibody, in which case the attachment may comprise a binding reaction between the antibody and the analyte (e.g., antibody and cell, antibody and protein, antibody and nucleic acid). In other cases, the unique identifier is a dye, in which case the attachment may comprise intercalation of the dye into the analyte molecule (such as intercalation into DNA or RNA) or binding to a probe labeled with the dye. In still other cases, the unique identifier may be a nucleic acid probe, in which case the attachment to the analyte may comprise a hybridization reaction between the nucleic acid and the analyte. In some cases, the reaction may comprise a chemical linkage between the identifier and the analyte. In other cases, the reaction may comprise addition of a metal isotope, either directly to the analyte or by a probe labeled with the isotope.

Often, the method comprises attaching oligonucleotide bar codes to nucleic acid analytes through an enzymatic reaction such as a ligation reaction. For example, the ligase enzyme may covalently attach a DNA bar code to fragmented DNA (e.g., high molecular-weight DNA). Following the attachment of the bar-codes, the molecules may be subjected to a sequencing reaction. However, other reactions may be used as well. For example, oligonucleotide primers containing bar code sequences may be used in amplification reactions (e.g., PCR, qPCR, reverse-transcriptase PCR, digital PCR, etc.) of the DNA template analytes, thereby producing tagged analytes. After assignment of bar codes to individual analytes, the contents of individual microwells may be recovered via the outlet port in the device for further analyses.

The unique identifiers (e.g., oligonucleotide bar-codes, antibodies, probes, etc.) may be introduced to the device randomly or nonrandomly. In some cases, they are introduced at an expected ratio of unique identifiers to microwells. For example, the unique identifiers may be loaded so that more than about 1, 2, 3, 4, 5, 6, 7, 8, 9, 10, 20, 50, 100, 500, 1000, 5000, 10000, or 200000 unique identifiers are loaded per microwell. In some cases, the unique identifiers may be loaded so that less than about 1, 2, 3, 4, 5, 6, 7, 8, 9, 10, 20, 50, 100, 500, 1000, 5000, 10000, or 200000 unique identifiers are loaded per microwell. In some cases, the average number of unique identifiers loaded per microwell is less than, or greater than, about 0.0001, 0.001, 0.01, 0.1, 1, 2, 3, 4, 5, 6, 7, 8, 9, 10, 20, 50, 100, 500, 1000, 5000, 10000, or 200000 unique identifiers per microwell.

The unique identifiers also may be loaded so that a set of one or more identical identifiers are introduced to a particular well. Such sets may also be loaded so that each microwell contains a different set of identifiers. For example, a population of microcapsules may be prepared such that a first microcapsule in the population comprises multiple copies of identical unique identifiers (e.g., nucleic acid bar codes, etc.) and a second microcapsule in the population comprises multiple copies of a unique identifier that differs from within the first microcapsule. In some cases, the population of microcapsules may comprise multiple microcapsules (e.g., greater than 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules), each containing multiple copies of a unique identifier that differs from that contained in the other microcapsules. In some cases, the population may comprise greater than 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules with identical sets of unique identifiers. In some cases, the population may comprise greater than 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules, wherein the microcapsules each comprise a different combination of unique identifiers. For example, in some cases the different combinations overlap, such that a first microcapsule may comprise, e.g., unique identifiers A, B, and C, while a second microcapsule may comprise unique identifiers A, B, and D. In another example, the different combinations do not overlap, such that a first microcapsule may comprise, e.g., unique identifiers A, B, and C, while a second microcapsule may comprise unique identifiers D, E, and F.

The unique identifiers may be loaded into the device at an expected or predicted ratio of unique identifiers per analyte (e.g., strand of nucleic acid, fragment of nucleic acid, protein, cell, etc.) In some cases, the unique identifiers are loaded in the microwells so that more than about 1, 2, 3, 4, 5, 6, 7, 8, 9, 10, 20, 50, 100, 500, 1000, 5000, 10000, or 200000 unique identifiers are loaded per individual analyte in the microwell. In some cases, the unique identifiers are loaded in the microwells so that less than about 1, 2, 3, 4, 5, 6, 7, 8, 9, 10, 20, 50, 100, 500, 1000, 5000, 10000, or 200000 unique identifiers are loaded per individual analyte in the microwell. In some cases, the average number of unique identifiers loaded per analyte is less than, or greater than, about 0.0001, 0.001, 0.01, 0.1, 1, 2, 3, 4, 5, 6, 7, 8, 9, 10, 20, 50, 100, 500, 1000, 5000, 10000, or 200000 unique identifiers per analyte. When more than one identifier is present per analyte, such identifiers may be copies of the same identifier, or multiple different identifiers. For example, the attachment process may be designed to attach multiple identical identifiers to a single analyte, or multiple different identifiers to the analyte.

The unique identifiers may be used to tag a wide range of analytes, including cells or molecules. For example, unique identifiers (e.g., bar code oligonucleotides) may be attached to whole strands of nucleic acids or to fragments of nucleic acids (e.g., fragmented genomic DNA, fragmented RNA). The unique identifiers (e.g., antibodies, oligonucleotides) may also bind to cells, include the external surface of a cell, a marker expressed on the cell or components within the cell such as organelles, gene expression products, genomic DNA, mitochondrial DNA, RNA, mRNA, or proteins. The unique identifiers also may be designed to bind or hybridize nucleic acids (e.g., DNA, RNA) present in permeabilized cells, which may or may not be otherwise intact.

The unique identifiers may be loaded onto the device either singly or in combination with other elements (e.g., reagents, analytes). In some cases, free unique identifiers are pooled with the analytes and the mixture is loaded into the device. In some cases, unique identifiers encapsulated in microcapsules are pooled with the analytes, prior to loading of the mixture onto the device. In still other cases, free unique identifiers are loaded into the microwells prior to, during (e.g., by separate inlet port), or following the loading of the analytes. In still other cases, unique identifiers encapsulated in microcapsules are loaded into the microwells prior to, concurrently with (e.g., by separate inlet port), or after loading of the analytes.

In many applications, it may be important to determine whether individual analytes each receive a different unique identifier (e.g., oligonucleotide bar code). If the population of unique identifiers introduced into the device is not significantly diverse, different analytes may possibly be tagged with identical identifiers. The devices disclosed herein may enable detection of analytes tagged with the same identifier. In some cases, a reference analyte may be included with the population of analytes introduced into the device. The reference analyte may be, for example, a nucleic acid with a known sequence and a known quantity. After the population of analytes is loaded and partitioned in the device, unique identifiers may be attached to the analytes, as described herein. If the unique identifiers are oligonucleotide bar codes and the analytes are nucleic acids, the tagged analytes may subsequently be sequenced and quantified. These methods may indicate if one or more fragments and/or analytes may have been assigned an identical bar code.

A method disclosed herein may comprise loading the device with the reagents necessary for the assignment of bar codes to the analytes. In the case of ligation reactions, reagents including, but not limited to, ligase enzyme, buffer, adapter oligonucleotides, a plurality of unique identifier DNA bar codes and the like may be loaded into the device. In the case of enrichment, reagents including but not limited to a plurality of PCR primers, oligonucleotides containing unique identifying sequence, or bar code sequence, DNA polymerase, DNTPs, and buffer and the like may be loaded into the device. The reagents may be loaded as free reagents or as reagents encapsulated in microcapsules.

C. Nucleic Acid Sequencing

Nucleic acid sequencing may begin with the physical partitioning of sample analytes into microwells at a particular density (e.g., about 1 analyte per microwell or other density described herein). When nucleic acid bar codes are assigned to individual analytes, it may then be possible to track individual molecules during subsequent steps such as subsequent amplification and/or sequencing steps, even if the analytes are later pooled together and treated en masse.

a. Nucleic Acid Phasing

The devices provided herein may be used to prepare analytes (e.g., nucleic acid analytes) in such a manner that enables phasing or linkage information to be subsequently obtained. Such information may allow for the detection of linked genetic variations in sequences, including genetic variations (e.g., SNPs, mutations, indels, copy number variations, transversions, translocations, inversions, etc.) that are separated by long stretches of nucleic acids. These variations may exist in either a cis or trans relationship. In cis relationships, two or more genetic variations may exist in the same polynucleic acid molecule or strand. In trans relationships, two or more genetic variations may exist on multiple nucleic acid molecules or strands.

A method of determining nucleic acid phasing may comprise loading a nucleic acid sample (e.g., a nucleic acid sample that spans a given locus or loci) into a device disclosed herein, distributing the sample such that at most one molecule of nucleic acid is present per microwell, and fragmenting the sample within the microwells. The method may further comprise attaching unique identifiers (e.g., bar codes) to the fragmented nucleic acids as described herein, recovering the nucleic acids in bulk, and performing a subsequent sequencing reaction on the samples in order to detect genetic variations, such as two different genetic variations. The detection of genetic variations tagged with two different bar codes may indicate that the two genetic variations are derived from two separate strands of DNA, reflecting a trans relationship. Conversely, the detection of two different genetic variations tagged with the same bar codes may indicate that the two genetic variations are from the same strand of DNA, reflecting a cis relationship.

Phase information may be important for the characterization of the analyte, particularly if the analyte derives from a subject at risk of, having, or suspected of a having a particular disease or disorder (e.g., hereditary recessive disease such as Cystic Fibrosis, cancer, etc.). The information may be able to distinguish between the following possibilities: (1) two genetic variations within the same gene on the same strand of DNA and (2) two genetic variations within the same gene but located on separate strands of DNA. Possibility (1) may indicate that one copy of the gene is normal and the individual is free of the disease, while possibility (2) may indicate that the individual has or will develop the disease, particularly if the two genetic variations are damaging to the function of the gene when present within the same gene copy. Similarly, the phasing information may also be able to distinguish between the following possibilities: (1) two genetic variations, each within a different gene on the same strand of DNA and (2) two genetic variations, each within a different gene but located on separate strands of DNA.

b. Cell-specific Information

The devices provided herein may be used to prepare cellular analytes in such a manner that enables cell-specific information to be subsequently obtained. Such information may enable detection of genetic variations (e.g., SNPs, mutations, indels, copy number variations, transversions, translocations, inversions, etc.) on a cell-by-cell basis, thereby enabling a determination of whether the genetic variation(s) are present in the same cell or two different cells.

A method of determining nucleic acid cell-specific information may comprise loading a cellular sample (e.g., a cellular sample from a subject) into a device disclosed herein, distributing the sample such that at most one cell is present per microwell, lysing the cells, and then tagging the nucleic acids within the cells with unique identifiers using a method described herein. In some cases, microcapsules comprising unique identifiers are loaded in the microwell array device (either before, during, or after the loading of the cellular analytes) in such a manner that each cell is contacted with a different microcapsule. The resulting tagged nucleic acids can then be pooled, sequenced, and used to trace the origin of the nucleic acids. Nucleic acids with identical unique identifiers may be determined to originate from the same cell, while nucleic acids with different unique identifiers may be determined to originate from different cells.

In a more specific example, the methods herein may be used to detect the distribution of oncogenic mutations across a population of cancer tumor cells. In this example, some of the cells may have a mutation, or amplification, of an oncogene (e.g., HER2, BRAF, EGFR, KRAS) on two strands of DNA (homozygous), while others may be heterozygous for the mutation, while still other cells may be wild-type and comprise no mutations or other variation in the oncogene. The methods described herein may be able to detect these differences, and also may enable quantification of the relative numbers of homozygous, heterozygous, and wild-type cells. Such information may be used to stage a particular cancer or to monitor the progression of the cancer over time.

In some examples, this disclosure provides methods of identifying mutations in two different oncogenes (e.g., KRAS and EGFR). If the same cell comprises genes with both mutations, this may indicate a more aggressive form of cancer. In contrast, if the mutations are located in two different cells, this may indicate that the cancer is more benign, or less advanced.

The following is another specific example of cell-specific sequence determination. In this example, a plurality of cells, such as from a tumor biopsy, is loaded into a device. Single cells from the sample are deposited into individual wells and labeled with a DNA bar code.

Loading of cells into a device may be achieved through non-random loading. Parameters for non-random loading of analytes, such as cells, may be understood using an interference function such that:

$$\text{"fraction multi-occupancy"} = 1 - \left[\left(1 - \frac{1}{N}\right) + \frac{P}{N}\right]^C$$

where

P=probability that a particular cell will attempt but not fit in the well (measure of interference)
N=number of wells
L=number of labels=barcodes
C=number of cells As part of sample preparation reactions, cells may be lysed and many subsequent reactions are possible, including RNA amplification, DNA amplification or antibody screening for different target proteins and genes in individual cells. After the reaction, the contents of the cells may be pooled together and could be further analyzed, such as by DNA sequencing. With each cell assigned a unique barcode, further analyses may be possible including but not limited to quantification of different gene levels or nucleic acid sequencing of individual cells. In this example, it may be determined whether the tumor comprises cells with different genetic backgrounds (e.g., cancer clones and subclones). The relative number of each type of cell may also be calculated.

c. Amplification Control

As disclosed herein, the device can be used for purposes of controlling for amplification errors, such as PCR errors. For example, a nucleic acid sample may be partitioned into the microwells of the device. Following partitioning, the sample may be subjected to a PCR amplification reaction within the microwells. The PCR products within a microwell may be tagged with the same unique identifier, using a method described herein. If the products are later sequenced and demonstrate sequence differences, differences among products with the same identifier can then be attributed to PCR error.

d. Gene-expression Products Analysis

In other applications, a device may be used to detect gene product (e.g., protein, mRNA) expression levels in a sample, often on a cell-by-cell basis. A sample may comprise individual cells, a pool of mRNA extract from cells, or other collection of gene products. In some instances, single cells may be loaded into microwells. In other instances, a pool of mRNA or other gene product may be loaded such that a desired quantity of mRNA molecules is loaded into individual microwells.

The methods provided herein may be particularly useful for RNA analysis. For example, using the methods provided herein, unique identifiers may be assigned to mRNA analytes either directly or to cDNA products of a reverse transcription reaction performed on the mRNA analytes. The reverse transcription reaction may be conducted within the microwells of the device following loading of the analytes. Reagents for the reaction may include but are not limited to reverse transcriptase, DNA polymerase enzyme, buffer, dNTPs, oligonucleotide primers, oligonucleotide primers containing bar code sequences and the like. One or more reagents may be loaded into microcapsules or loaded freely in solution into the device or a combination thereof. Sample preparation may then be conducted, such as by fragmenting the cDNA and attaching unique identifiers to the fragments.

After sample preparation and recovery, the nucleic acid products of the reaction may be further analyzed, such as by sequencing.

Additionally, a device may be used to characterize multiple cell markers, similar to a flow cytometer. Any cell marker may be characterized, including cell-surface markers (e.g., extracellular proteins, transmembrane markers) and markers located within the internal portion of a cell (e.g., RNA, mRNA, microRNA, multiple copies of genes, proteins, alternative splicing products, etc.). For example, cells may be partitioned within the device, as described herein, so that at most one cell is present within a microwell. Cell markers such as nucleic acids (e.g., RNA) may be extracted and/or fragmented prior to being labeled with a unique identifier (e.g., molecular bar code). Or, alternatively, the nucleic acids may be labeled with a unique identifier without being extracted and/or fragmented. The nucleic acids may then be subjected to further analysis such as sequencing reactions designed to detect multiple gene expression products. Such analysis may be useful in a number of fields. For example, if the starting cells are immune cells (e.g., T cells, B cells, macrophages, etc.), the analysis may provide information regarding multiple expressed markers and enable immunophenotyping of the cells, for example by identifying different CD markers of the cells (e.g., CD3, CD4, CD8, CD19, CD20, CD 56, etc.). Such markers can provide insights into the function, character, class, or relative maturity of the cell. Such markers can also be used in conjunction with markers that are not necessarily immunophenotyping markers, such as markers of pathogenic infection (e.g., viral or bacterial protein, DNA, or RNA). In some cases, the device may be used to identify at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 200, 500, 700, 1000, 5000, 10000, 50000, or 100000 different gene expression products or other form of cellular markers on a single-cell basis. Often, such methods do not comprise use of dyes or probes (e.g., fluorescent probes or dyes).

Gene expression product analysis may be useful in numerous fields including immunology, cancer biology (e.g., to characterize the existence, type, stage, aggressiveness, or other characteristic of cancerous tissue), stem cell biology (e.g., in order to characterize the differentiation state of a stem cell, potency of a stem cell, cellular type of a stem cell, or other features of a stem cell), microbiology, and others. The gene expression analysis may also be used in drug screening applications, for example to evaluate the effect of a particular drug or agent on the gene expression profile of particular cells.

VII. Terminology

The terminology used therein is for the purpose of describing particular embodiments only and is not intended to be limiting of a device of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a device of this disclosure are described above with reference to example applications for illustration. It should be understood that numerous specific details, relationships, and methods are set forth to provide a full understanding of a device. One having ordinary skill in the relevant art, however, will readily recognize that a device can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another embodiment includes from the one particular value and/or to the other particular value Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

The term microwell array, as used herein, generally refers to a predetermined spatial arrangement of microwells. Microwell array devices that comprise a microcapsule may also be referred to as "microwell capsule arrays." Further, the term "array" may be used herein to refer to multiple arrays arranged on a surface, such as would be the case where a surface has multiple copies of an array. Such surfaces bearing multiple arrays may also be referred to as "multiple arrays" or "repeating arrays."

EXAMPLE 1

Single cell DNA Sequencing

A microwell capsule array is prepared to perform nucleic acid sequencing on individual human B-cells taken from a blood sample. Approximately 15,000 cells are harvested and used for loading into the device. A device of this disclosure and containing 150,000 microwells is used. Each well is cylindrical in shape having a diameter of 125 um and a height of 125 um, allowing at most 1 capsule to be loaded per well. Microcapsules made through emulsion polymerization with a PNIPAM hydrogel shell wall are created such that the microcapsules have a diameter of 100 um for loading in the device. The microcapsules are created such that the PNIPAM shell contains magnetic iron particles. The outer surface of the shell is then chemically coupled to a antibody specific to a transmembrane B cell receptor on the outside of a B cell.

During the preparation process of capsules, reagents are simultaneously loaded into the capsules. Reagents necessary for cell lysis and labeling individual DNA strands of the cells with DNA barcodes are loaded into capsules. Reagents for cell lysis include a mild non-ionic detergent, buffer and salt. Reagents for the addition of DNA bar codes to genomic DNA included restriction enzymes, ligase, and >10,000,000 unique DNA oligonucleotides are loaded into capsules. Capsules are designed to be sensitive to rupture at greater than 65 C.

Capsules are prepared to be applied to the microcapsule array. The array is placed on a magnetic temperature controlled hot plate. Microcapsules are added to a sample of B cells such that one B cell is able to bind to one capsule. Capsule-cell conjugates are applied in aqueous carrier solution in a quantity in excess to the relative number of wells. Gentle pipetting of capsules-cells into the inlet port followed by application of a vacuum manifold to the outlet port distributes the capsules throughout the device. A magnetic field is applied through the plate. Excess capsule-cell solution is removed via pipetting through the outlet port. Each capsule-cell conjugate is trapped and positioned in individual wells via the magnetic field.

After the cells and capsules are loaded in the device, a carrier oil (or sealing fluid) is applied to the device to remove any excess aqueous solution bridging adjacent microwells. The carrier oil applied to the inlet and excess oil is recovered at the outlet with a vacuum manifold. After the carrier oil is applied, the inlet and outlet ports are sealed with tape.

The device is then heated, via the magnetic temperature controlled hot plate, to a temperature of 70 C. for 10 min to allow for capsule rupture and cell lysis. The hot plate is then switched to 37 C., for restriction and ligation, for up to 1 hour.

After the sample preparation reaction is completed, the contents of the wells are recovered. The inlet and outlet ports of the device are unsealed and nitrogen gas is applied to the device to flush out the individual components of the microwells. The sample is collected in bulk via a pipette at the outlet port, while the magnetic field retains ruptured capsule shells in individual microwells.

The sample is then sequenced using a multiplex sequencing strategy known in the art. Bar coding of individual cells allows for sequencing information to be gained for individual cells rather than as an average of multiple cells. Based upon the number of cells sequenced and bar codes assigned, SNP cell-specific information is gained. Moreover, the number of reads for individual bar codes can be counted to provide insight into the distribution of different types of cells with varying genetic backgrounds, within the original population of B cells.

EXAMPLE 2

DNA Single Strand Sequencing

A microwell capsule array is prepared to perform nucleic acid sequencing on individual strands of DNA isolated from a population of human skin cells. Cells are lysed using detergent and heat and approximately 15,000 copies of diploid DNA are precipitated via chloroform/ethanol extraction. A resuspension of DNA is loaded into the device with approximately 10,000 copies of haploid DNA. A device of this disclosure, with 300,000 microwells is used. Each well is cylindrical in shape having a diameter of 125 um and a height of 125 um, allowing at most 1 capsule to be loaded per well. Microcapsules made through emulsion polymerization with a PNIPAM hydrogel shell wall are created to a specification of a sphere with a diameter of 100 um for loading into the device.

During the preparation of the microcapsules, reagents are simultaneously loaded into the capsules. The reagents include reagents necessary for labeling individual DNA strands with DNA barcodes, including restriction enzymes, ligase, and >10,000,000 unique DNA oligonucleotides. Capsules designed to be sensitive to rupture at greater than 65 C. are used for the encapsulation.

Capsules are applied aqueous carrier solution in an excess to the relative number of wells. Gentle pipetting of capsules into the inlet followed by application of a vacuum manifold to the outlet distributed the capsules throughout the device.

After excess capsule solution is removed, a suspension of DNA in buffer is applied to the device in a similar fashion as the capsules.

After the DNA strands and capsules are loaded in the device, a carrier oil is applied to the device to remove any excess aqueous solution bridging adjacent microwells. The carrier oil is applied to the inlet port and excess oil is recovered at the outlet port with a vacuum manifold. After the carrier oil is applied, the inlet and outlet ports are sealed with tape.

The device is then placed on a temperature controlled hot plate and heated to temperature of 70 C. for 10 min to allow for capsule rupture. Reagents are released into the sample preparation reaction. The hot plate is then switched to 37 C., for restriction and ligation, for up to 1 hour.

After the sample preparation reaction is completed, the inlet and outlet ports of the device are unsealed and nitrogen gas is applied to the device to flush out the individual components of the microwells. The sample products, en bulk, are collected via pipette at the outlet port.

The sample is then sequenced to sufficient coverage (e.g., 500) using a multiplex sequencing strategy known in the art. Bar coding of individual DNA strands allows for sequencing information to be gained from individual strands rather than as an average of entire sample of DNA. Based upon the number of DNA strands sequenced and bar codes assigned, SNP phasing/haplotyping information is gained and many repetitive regions of DNA can be resolved. In addition, a substantial boost in accuracy can be gained by discarding mutations that appear randomly with respect to haplotypes, as those are likely to be sequencing errors.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A composition for use in barcoding nucleic acid molecules, comprising:
   a population of at least 1,000 gel beads comprising a plurality of nucleic acid barcode molecules,
   wherein a given gel bead of said at least 1,000 gel beads comprises at least 1,000 nucleic acid barcode molecules of said plurality of nucleic acid barcode molecules,
   wherein at least (i) a first subset of said at least 1,000 nucleic acid barcode molecules is coupled to an interior surface of said given gel bead, and (ii) a second subset of said at least 1,000 nucleic acid barcode molecules is coupled to an outer surface of said given gel bead, and
   wherein each of said at least 1,000 nucleic acid barcode molecules comprises an identical barcode sequence that differs from barcode sequences of barcode molecules comprised in other gel beads of said at least 1,000 gel beads.

2. The composition of claim 1, wherein said at least 1,000 gel beads are at least 100,000 gel beads.

3. The composition of claim 1, wherein said given gel bead is coupled to at least 100,000 of said plurality of nucleic acid barcode molecules, wherein each of said at least 100,000 nucleic acid barcode molecules comprises said identical barcode sequence.

4. The composition of claim 1, wherein said given gel bead is coupled to at least 1,000,000 of said plurality of nucleic acid barcode molecules, wherein each of said at least 1,000,000 nucleic acid barcode molecules comprises said identical barcode sequence.

5. The composition of claim 1, wherein said first subset of said at least 1,000 nucleic acid barcode molecules is covalently bonded to said interior surface of said given gel bead.

6. The composition of claim 1, wherein said first subset of said at least 1,000 nucleic acid barcode molecules is reversibly coupled to said interior surface of said given gel bead.

7. The composition of claim 6, wherein said first subset of said at least 1,000 nucleic acid barcode molecules is reversibly coupled to said interior surface of said given gel bead through chemical cross-linkers.

8. The composition of claim 7, wherein said chemical cross-linkers are degradable by an acid or a reducing agent.

9. The composition of claim 6, wherein said first subset of said at least 1,000 nucleic acid barcode molecules is reversibly coupled to said interior surface of said given gel bead through disulfide bonds.

10. The composition of claim 1, wherein said plurality of nucleic acid barcode molecules is releasable from said at least 1,000 gel beads.

11. The composition of claim 1, wherein said at least 1,000 gel beads have substantially uniform cross-sectional sizes.

12. The composition of claim 1, wherein said given gel bead has a cross-sectional dimension of at least 10 micrometers.

13. The composition of claim 1, wherein said at least 1,000 gel beads are degradable upon application of a stimulus.

14. The composition of claim 1, wherein said at least 1,000 gel beads are at least 1,000,000 gel beads.

15. The composition of claim 1, wherein said at least 1,000 nucleic acid barcode molecules comprise immobilization sequence regions.

16. The composition of claim 1, wherein said given gel bead comprises cross-linked polymeric precursors.

17. A composition for use in barcoding a nucleic acid molecule, comprising:
   at least 1,000 nucleic acid barcode molecules coupled to a gel bead, wherein said gel bead is degradable upon application of a stimulus,
   wherein at least a subset of said at least 1,000 nucleic acid barcode molecules is coupled to an interior surface of said gel bead, and
   wherein each of said at least 1,000 nucleic acid barcode molecules coupled to said gel bead comprises an identical barcode sequence.

18. The composition of claim 1, wherein said given gel bead is coupled to at least 10,000,000 of said plurality of nucleic acid barcode molecules.

19. The composition of claim 17, wherein said gel bead comprises cross-linked polymeric precursors.

20. The composition of claim 17, wherein said gel bead is coupled to at least 100,000 nucleic acid barcode molecules, wherein each of said at least 100,000 nucleic acid barcode molecules comprises said identical barcode sequence.

21. The composition of claim 17, wherein said at least a subset of said at least 1,000 nucleic acid barcode molecules is covalently bonded to said interior surface of said gel bead.

22. The composition of claim 17, wherein said at least a subset of said at least 1,000 nucleic acid barcode molecules is reversibly coupled to said interior surface of said gel bead.

23. The composition of claim 22, wherein said at least a subset of said at least 1,000 nucleic acid barcode molecules is reversibly coupled to said interior surface of said gel bead through chemical cross-linkers.

24. The composition of claim 23, wherein said chemical cross-linkers are degradable by an acid.

25. The composition of claim 22, wherein said at least a subset of said at least 1,000 nucleic acid barcode molecules is reversibly coupled to said interior of said gel bead through disulfide bonds.

26. The composition of claim 23, wherein said chemical cross-linkers are degradable by a reducing agent.

27. The composition of claim 17, wherein an additional subset of said at least 1,000 nucleic acid barcode molecules is coupled to an outer surface of said gel bead.

28. The composition of claim 17, wherein said at least 1,000 nucleic acid barcode molecules are releasable from said gel bead.

29. The composition of claim 17, wherein said at least 1,000 nucleic acid barcode molecules comprise immobilization sequence regions.

30. The composition of claim 17, wherein said at least 1,000 nucleic acid barcode molecules is at least 10,000,000 nucleic acid barcode molecules coupled to said gel bead.

* * * * *

UNITED STATES PATENT AND TRADEMARK OFFICE
CERTIFICATE OF CORRECTION

PATENT NO. : 10,053,723 B2
APPLICATION NO. : 15/719459
DATED : August 21, 2018
INVENTOR(S) : Benjamin Hindson et al.

It is certified that error appears in the above-identified patent and that said Letters Patent is hereby corrected as shown below:

In the Claims

At Column 33, Line 66, please change "1000nucleic" to --1000 nucleic--.

Signed and Sealed this
Sixth Day of November, 2018

Andrei Iancu
*Director of the United States Patent and Trademark Office*